United States Patent
Yigang et al.

(10) Patent No.: US 10,976,422 B2
(45) Date of Patent: Apr. 13, 2021

(54) ULTRASOUND IMAGING METHODS AND SYSTEMS

(71) Applicant: Shenzhen Mindray Bio-Medical Electronics Co., Ltd., Shenzhen (CN)

(72) Inventors: Du Yigang, Shenzhen (CN); Fan Rui, Shenzen (CN); Li Yong, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 417 days.

(21) Appl. No.: 15/632,176

(22) Filed: Jun. 23, 2017

(65) Prior Publication Data
US 2017/0285156 A1    Oct. 5, 2017

Related U.S. Application Data

(63) Continuation of application No. PCT/CN2015/072022, filed on Jan. 30, 2015.

(51) Int. Cl.
*G01S 7/52* (2006.01)
*A61B 8/06* (2006.01)
(Continued)

(52) U.S. Cl.
CPC ............ *G01S 7/52085* (2013.01); *A61B 8/00* (2013.01); *A61B 8/06* (2013.01); *G01S 7/5206* (2013.01);
(Continued)

(58) Field of Classification Search
CPC ............ G01S 15/8984; G01S 7/52085; G01S 15/8993; G01S 15/8927; G01S 7/52071;
(Continued)

(56) References Cited

U.S. PATENT DOCUMENTS

| 2007/0083099 A1* | 4/2007 | Henderson | A61B 5/02007 600/407 |
| 2011/0196237 A1* | 8/2011 | Pelissier | A61B 8/06 600/454 |

(Continued)

FOREIGN PATENT DOCUMENTS

| CN | 101357069 A | 2/2009 |
| CN | 101828929 A | 9/2010 |

(Continued)

*Primary Examiner* — Hien N Nguyen
(74) *Attorney, Agent, or Firm* — Kory D. Christensen

(57) ABSTRACT

An ultrasound imaging system may include a probe, a transmitting circuit which may excite the probe to transmit ultrasound beams towards a scanning target in at least three ultrasound propagation directions; a receiving circuit and a beamforming unit which may respectively receive the echoes of the ultrasound beams in the ultrasound propagation directions to obtain the echo signals in each of the ultrasound propagation directions; a data processing unit which may obtain velocity vectors of target points in the scanning target using the echo signals in each of the ultrasound propagation directions and obtain ultrasound images of at least a portion of the scanning target using the echo signals; and a display which may display the velocity vectors and the ultrasound images.

33 Claims, 16 Drawing Sheets

(51) Int. Cl.
*G01S 15/89* (2006.01)
*A61B 8/00* (2006.01)
*A61B 8/08* (2006.01)

(52) U.S. Cl.
CPC ...... *G01S 7/52071* (2013.01); *G01S 7/52074* (2013.01); *G01S 15/8922* (2013.01); *G01S 15/8925* (2013.01); *G01S 15/8927* (2013.01); *G01S 15/8979* (2013.01); *G01S 15/8984* (2013.01); *G01S 15/8993* (2013.01); *A61B 8/0891* (2013.01); *A61B 8/483* (2013.01)

(58) Field of Classification Search
CPC ............. G01S 15/8922; G01S 7/52074; G01S 15/8925; G01S 7/5206; G01S 15/8979; A61B 8/06; A61B 8/00; A61B 8/0891; A61B 8/483
See application file for complete search history.

(56) References Cited

U.S. PATENT DOCUMENTS

| | | | | |
|---|---|---|---|---|
| 2012/0095332 | A1* | 4/2012 | Nitta | A61B 5/02007 600/437 |
| 2013/0165777 | A1* | 6/2013 | Kim | G01S 15/8984 600/437 |
| 2013/0172745 | A1* | 7/2013 | Choi | G01S 15/8984 600/441 |
| 2015/0094582 | A1* | 4/2015 | Tanaka | A61B 8/06 600/441 |
| 2016/0361040 | A1* | 12/2016 | Tanaka | A61B 8/06 |

FOREIGN PATENT DOCUMENTS

| | | |
|---|---|---|
| CN | 103181789 A | 7/2013 |
| CN | 104168835 A | 11/2014 |
| WO | WO0068697 A1 | 11/2000 |

* cited by examiner

ULTRASOUND IMAGING METHODS AND SYSTEMS

CROSS-REFERENCE TO RELATED APPLICATIONS

This application is a continuation of PCT App. No. PCT/CN2015/072022, filed Jan. 30, 2015, for ULTRASOUND IMAGING METHOD AND SYSTEM, which is incorporated herein by reference.

TECHNICAL FIELD

The present disclosure relates to medical ultrasound imaging, and more particularly to an ultrasound imaging method and system by which velocity vectors of target points can be obtained.

BACKGROUND

In medical ultrasound imaging, it is beneficial to obtain velocity vectors of moving objects in an organism (e.g., moving tissues, blood or other fluid, etc.). However, by traditional Doppler ultrasound imaging, only a velocity in the transmitting direction of the ultrasound waves (i.e., the propagation direction of the ultrasound waves) can be obtained. Even if a velocity vector can be obtained by synthesizing two velocities in two angles, it can only represent the velocity of fluid in a two-dimensional plane, but the magnitude and direction of the actual velocity in a three-dimensional space cannot be truly provided. Furthermore, in a traditional method for measuring a velocity of a moving object using focused ultrasound waves, since the time resolution is limited and the transmitting of the focused ultrasound waves is performed line by line, it is hard to ensure the spatial continuity of the velocity measurement, especially when a moving object with high velocity is measured.

SUMMARY

The present disclosure provides ultrasound imaging methods and systems.

DETAILED DESCRIPTION

Figure 1:
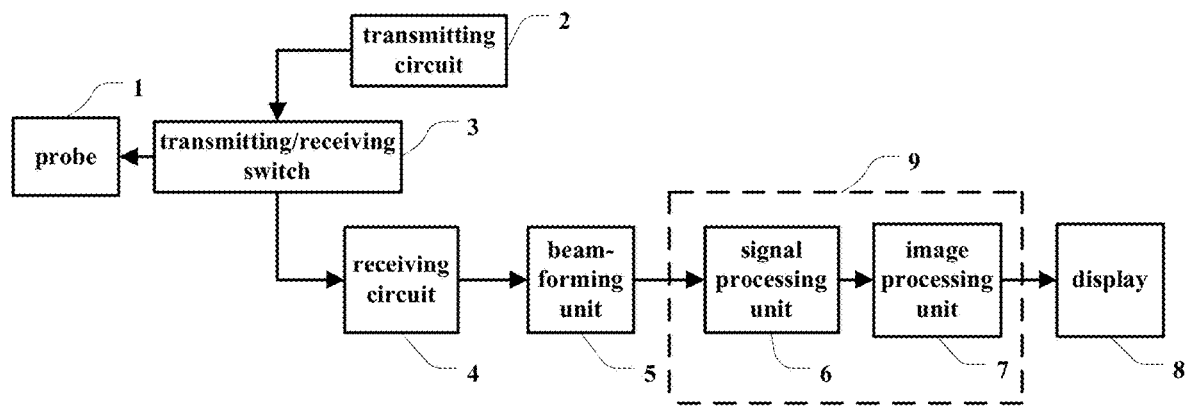
FIG. 1 is a block diagram of an ultrasound imaging system.

The present disclosure provides an ultrasound imaging method and system by which the velocity vector of the target point can be obtained, enabling the obtained velocity vector to be closer to the flow direction of actual flow.

In one embodiment, a transmitting circuit may excite a probe to transmit ultrasound beams towards a scanning target in at least three ultrasound propagation directions. A receiving circuit may receive, via the probe, echoes of the ultrasound beams and convert the echoes into electric signals, and a beamforming unit may beamform the electric signals to obtain at least three groups of echo signals, where each group of echo signals may be derived from ultrasound beams transmitted in one ultrasound propagation direction.

A data processing unit may calculate at least three velocity components of a target point in the scanning target using the at least three groups of echo signals, where one velocity component of the target point may be calculated using one group of echo signals of the at least three groups of echo signals. The data processing unit may also synthesize a velocity vector of the target point using the at least three velocity components, where at least three ultrasound propagation directions corresponding to the at least three groups of echo signals used for calculating the at least three velocity components may not be in a same plane. Furthermore, the data processing unit may also obtain an ultrasound image of at least a portion of the scanning target. A display may display the ultrasound image and the velocity vector.

In one embodiment, a transmitting circuit may excite a probe to transmit plane ultrasound beams towards a scanning target in at least three ultrasound propagation directions. A receiving circuit may receive, via the probe, echo signals of the plane ultrasound beams and convert the echoes into electric signals, and a beamforming unit may beamform the electric signals to obtain at least three groups of plane beam echo signals, where each group of plane beam echo signals may be derived from plane ultrasound beams transmitted in one ultrasound propagation direction.

A data processing unit may calculate at least three velocity components of a target point in the scanning target using the at least three groups of plane beam echo signals, where one velocity component of the target point may be calculated using one group of plane beam echo signals of the at least three groups of plane beam echo signals. The data processing unit may also synthesize a velocity vector of the target point using the at least three velocity components, where at least three ultrasound propagation directions corresponding to the at least three groups of plane beam echo signals used for calculating the at least three velocity components may not be in a same plane.

The transmitting circuit may further excite the probe to transmit focused ultrasound beams towards the scanning target. The receiving circuit may further receive, via the probe, echoes of the focused ultrasound beams and convert the echoes into electric signals, and the beamforming unit may further beamform the electric signals to obtain focused ultrasound beam echo signals. The data processing unit may obtain an ultrasound image of at least a portion of the scanning target using the focused ultrasound beam echo signals. A display may display the ultrasound image and the velocity vector.

In one embodiment, an ultrasound imaging system may include a probe, a transmitting circuit, a receiving circuit, a beamforming unit, a data processing unit and a display. The transmitting circuit may excite the probe to transmit ultrasound beams towards a scanning target in at least three ultrasound propagation directions. The receiving circuit may receive, via the probe, echo signals of the plane ultrasound beams and convert the echoes into electric signals. The beamforming unit may beamform the electric signals to obtain at least three groups of echo signals, where each group of echo signals may be derived from ultrasound beams transmitted in one ultrasound propagation direction.

The data processing unit may calculate at least three velocity components of a target point in the scanning target using the at least three groups of echo signals, where one velocity component of the target point may be calculated using one group of echo signals of the at least three groups of echo signals. The data processing unit may also synthesize a velocity vector of the target point using the at least three velocity components, where at least three ultrasound propagation directions corresponding to the at least three groups of echo signals used for calculating the at least three velocity components may not be in a same plane. The data processing unit may further obtain an ultrasound image of at least a portion of the scanning target. The display may display the ultrasound image and the velocity vector.

An ultrasound imaging system may obtain an approximate real velocity vector of the target point in a real three-dimensional space, and the velocity vector may be closer to the real flow direction of the flow in the three-dimensional space. Further, the accuracy and real-time of the velocity vector may also be increased. In the ultrasound imaging methods provided by one embodiment, both the plane ultrasound beams and the focused ultrasound beams may be used during the imaging. The plane ultrasound beams may be used to obtain the velocity vectors, and thereby the advantage of the high frame rate of plane ultrasound beam imaging may be fully utilized to satisfy the high frame rate requirement for fluid velocity measurement using ultrasound imaging. The focused ultrasound beams may be used to obtain the ultrasound images of the scanning target, and thereby the advantages of high signal-to-noise ratio of the echo signal, high quality of obtained ultrasound images and high lateral resolution of focused ultrasound beam imaging may be fully used to obtain better images for observation of the user.

FIG. 1 is a block diagram of an ultrasound imaging system according to one embodiment. As shown in FIG. 1, the ultrasound imaging system may generally include a probe 1, a transmitting circuit 2, a transmitting/receiving switch 3, a receiving circuit 4, a beamforming unit 5, a signal processing unit 6, an image processing unit 7, and a display 8.

In an ultrasound imaging process, the transmitting circuit 2 may transmit transmitting pulses, which have been delay focused and have certain amplitude and polarity, to the probe 1 through the transmitting/receiving switch 3. The probe 1 may be excited by the transmitting pulses and thereby transmit ultrasound waves towards a scanning target (e.g., an organ within a human or animal body, a blood vessel within a tissue or other vessel within an organism in which fluid flows, etc.), receive ultrasound echoes which are reflected by a target region and carry information related to the scanning target after a certain time interval, and convert the ultrasound echoes into electric signals. The receiving circuit may receive the electric signals converted by the probe 1 to obtain ultrasound echo signals and send the ultrasound echo signals to the beamforming unit 5. The beamforming unit 5 may perform processing, such as focus delaying, weighting, and channel summing, etc., on the ultrasound echo signals and then send the ultrasound echo signals to the signal processing unit 6, where related signal processing procedures will be performed.

The ultrasound echo signals processed by the signal processing unit 6 may be sent to the image processing unit 7, where the ultrasound echo signals may be processed in different ways according to the imaging mode desired by the user in order to obtain image data in different mode. Thereafter, the image data may undergo the processing, such as logarithmic compression, dynamic range adjustment, and digital scan conversion, etc., to form ultrasound images of different modes, such as B images, C images or D images, etc.

The ultrasound images generated by the image processing unit 7 may be sent to the display 8 to be displayed.

The probe 1 may generally include an array of a plurality of transducers. Each time the ultrasound waves are transmitted, all or a part of the transducers of the probe 1 may be used. In this case, each or each part of the used transducers may be respectively excited by the transmitting pulse and respectively transmit ultrasound wave. The ultrasound waves transmitted by the transducers may superpose with each other during the propagation such that a resultant ultrasound beam transmitted to the scanning target can be formed. The direction of the resultant ultrasound beam may be the "ultrasound propagation direction" mentioned in the present disclosure.

The used transducers may be simultaneously excited by the transmitting pulses. Alternatively, a certain time delay may exist between the excitation times of the used transducers by the transmitting pulses. By controlling the time delay between the excitation times of the used transducers by the transmitting pulses, the propagation direction of the resultant ultrasound beam can be changed, as described in detail below.

By controlling the time delay between the excitation times of the used transducers by the transmitting pulses, it may be possible that the ultrasound waves transmitted by the used transducers neither focus nor completely diffuse during the propagation, but form a plane wave which is substantially planar as a whole. In the present disclosure, such plane wave without a focus may be referred to as a "plane ultrasound beam".

Figure 4:
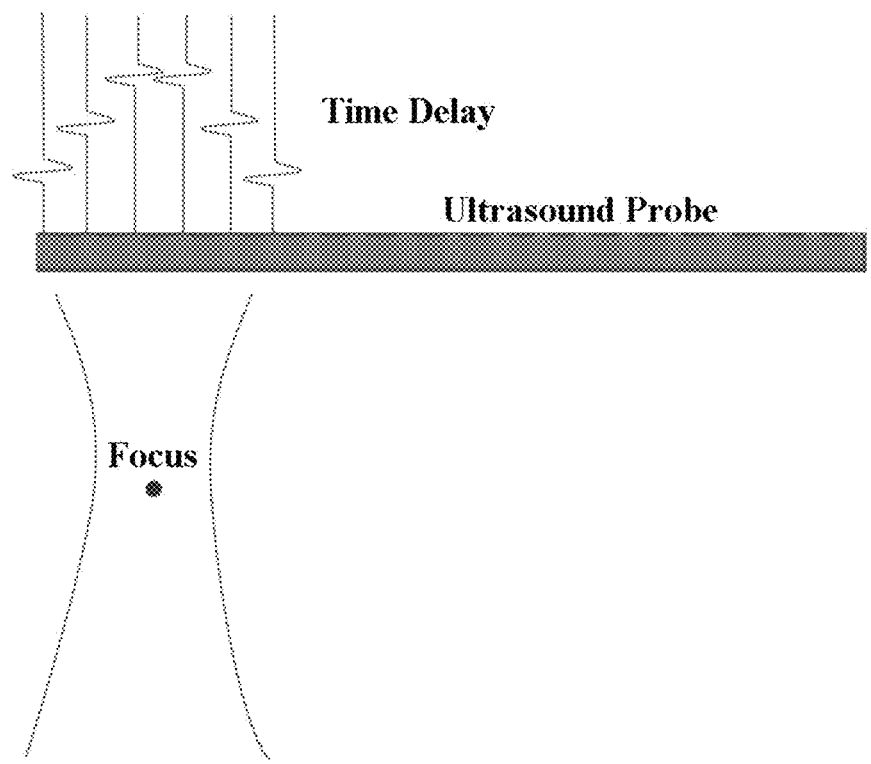
FIG. 4 schematically shows a focused ultrasound beam.

In one embodiment, by controlling the time delay between the excitation times of the used transducers by the transmitting pulses, it may also be possible that the ultrasound waves transmitted by the transducers superpose at a predetermined position such that the strength of the ultrasound waves at the predetermined position is maximum, i.e., such that the ultrasound waves transmitted by the transducers may be "focused" at the predetermined position. Such predetermined position may be referred to as a "focus". In this case, the obtained resultant ultrasound beam may be a beam focused at the focus, which may be referred to as a "focused ultrasound beam" in the present disclosure. For example, FIG. 4 schematically shows the transmitting of a focused ultrasound beam. Here, the used transducers (in FIG. 4, only a part of the transducers of the probe 1 are used) may work with a predetermined transmission time delay (i.e., a predetermined time delay may exist between the excitation times of the used transducers by the transmitting pulses) and the ultrasound waves transmitted by the transducers may be focused at the focus to form the focused ultrasound beam.

Figure 5:
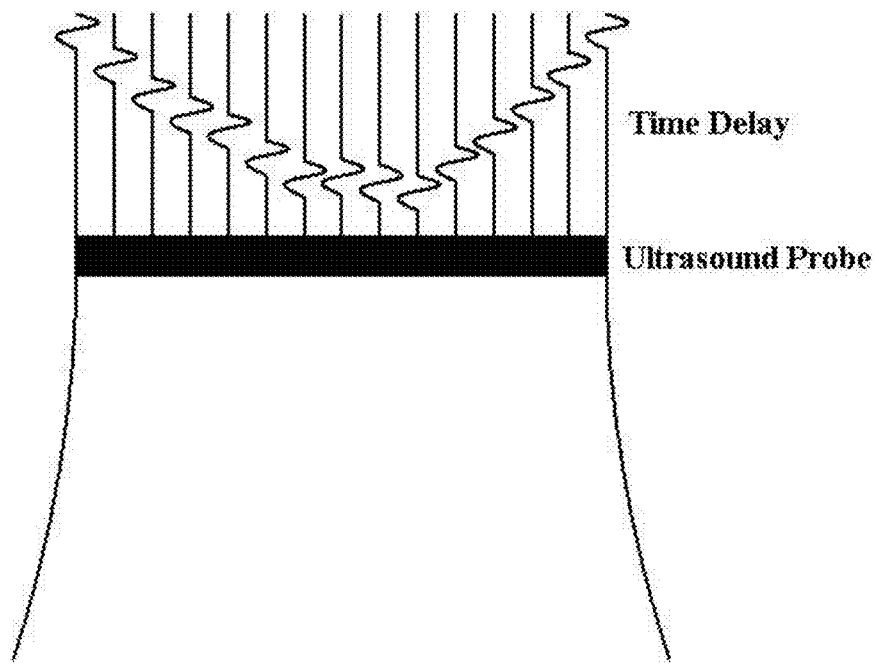
FIG. 5 schematically show a diffusion ultrasound beam.

In one embodiment, by controlling the time delay between the excitation times of the used transducers by the transmitting pulses, it may also be possible that the ultrasound waves transmitted by the used transducers diffuse during the propagation to form a diffusion wave which is substantially diffuse as a whole. In the present disclosure, such diffused ultrasound wave may be referred to as a "diffusion ultrasound beam". An example of the diffusion ultrasound beam is shown in FIG. 5.

Figure 2:
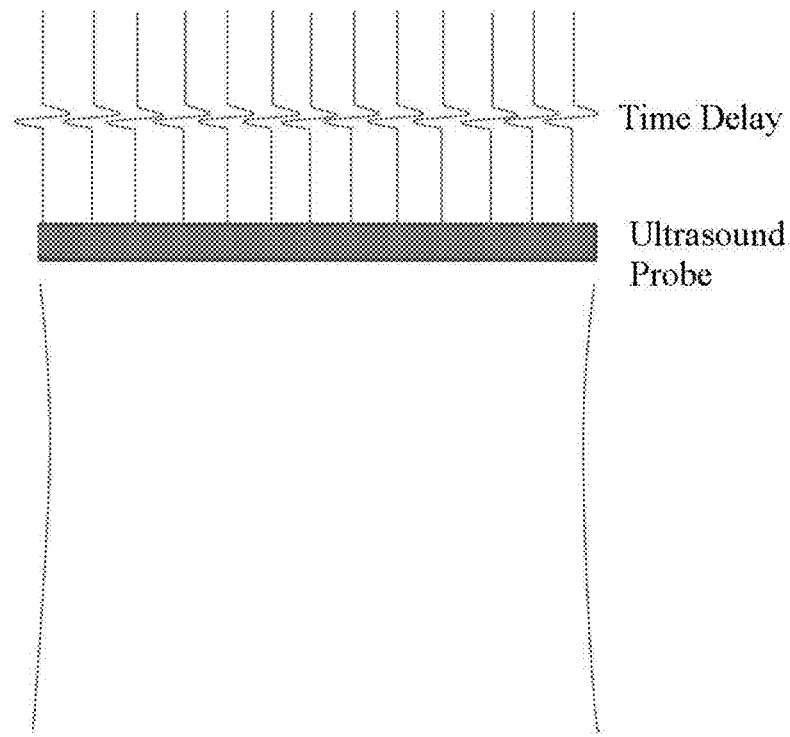
FIG. 2 schematically shows a plane ultrasound beam transmitted vertically.
Figure 3:
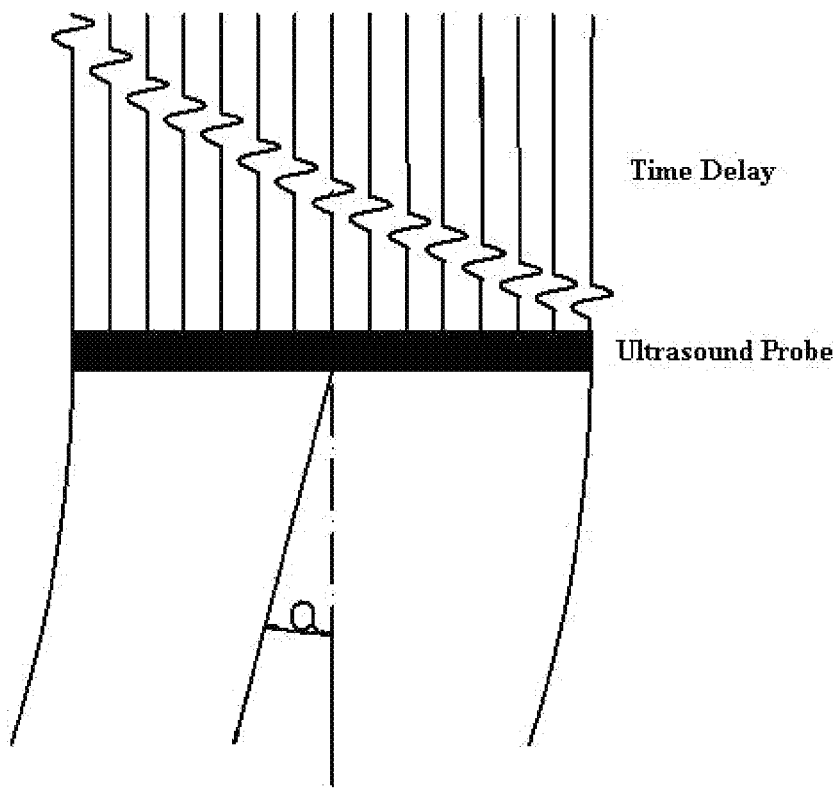
FIG. 3 schematically shows a steered plane ultrasound beam.

In the case that a plurality of transducers linearly arranged are excited simultaneously by electronic pulses, the transducers will simultaneously transmit ultrasound waves and the propagation direction of the resultant ultrasound beam will be the same as the normal direction of the plane on which the transducers are arranged. For example, for the plane beam vertically transmitted shown in FIG. 2, there is no time delay between the used transducers (i.e., there is no time delay between the excitation times of the transducers by the transmitting pulses) and the transducers are excited simultaneously. The ultrasound beam formed thereby is a plane beam, i.e., a plane ultrasound beam. The propagation direction of this plane ultrasound beam is substantially perpendicular to the surface of the probe 1 from which the ultrasound waves are transmitted, i.e., the angle between the propagation direction of the resultant ultrasound beam and the normal direction of the plane on which the transducers are arranged is zero degrees. However, in the case that there is time delay between the excitation pulses applied to the transducers, the transducers will successively transmit ultrasound waves according to the time delay, and there will be an certain angle between the propagation direction of the resultant ultrasound beam and the normal direction of the plane on which the transducers are arranged. This angle is the steered angle of the resultant beam. By changing the time delay, the magnitude of the steered angle, and the direction of the steering in the scanning plane of the resultant beam with respect to the normal direction of the plane on which the transducers are arranged, of the resultant beam may be adjusted. For example, FIG. 3 schematically shows a plane beam with a steered angle. In this case, there is a predetermined time delay between the used transducers (i.e., between the excitation times of the used transducers by the transmitting pulses), and the transducers are excited in a predetermined order by the transmitting pulses. The ultrasound beam generated thereby is a plane beam, i.e. a plane ultrasound beam, and there is an angle (the angle a in FIG. 3) between the propagation direction of this plane ultrasound beam and the normal direction of the plane on which the transducers of the probe 1 are arranged. This angle is the steered angle of the plane ultrasound beam and may be adjusted by changing the time delay.

Similarly, regardless of the plane ultrasound beam, the focused ultrasound beam or the diffusion ultrasound beam, the "steered angle" of the resultant beam formed between the direction of the resultant beam and the normal direction of the plane on which the transducers are arranged can be adjusted by adjusting the time delay between the excitation times of the used transducers by the transmitting pulses. The "resultant beam" herein may be the plane ultrasound beam, the focused ultrasound beam of the diffusion ultrasound beam mentioned above.

Figure 6A:
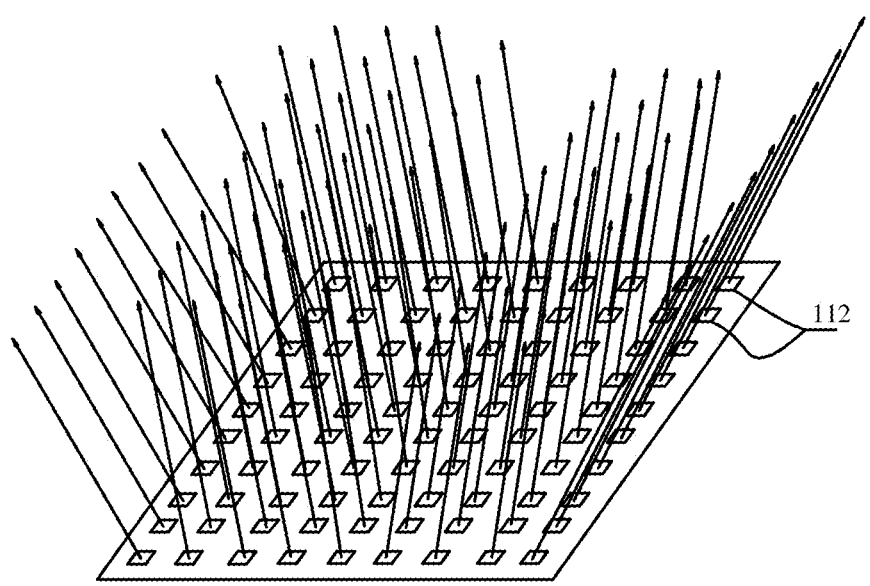
FIG. 6A schematically shows the transducers of a two-dimensional array probe.
Figure 6B:
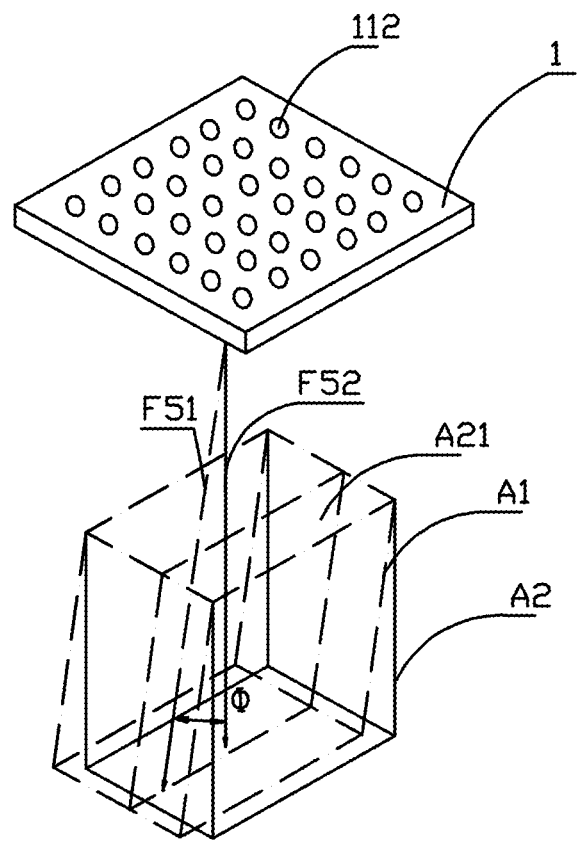
FIG. 6B schematically shows a three-dimensional scanning in an ultrasound propagation direction using the two-dimensional array probe.
Figure 6C:
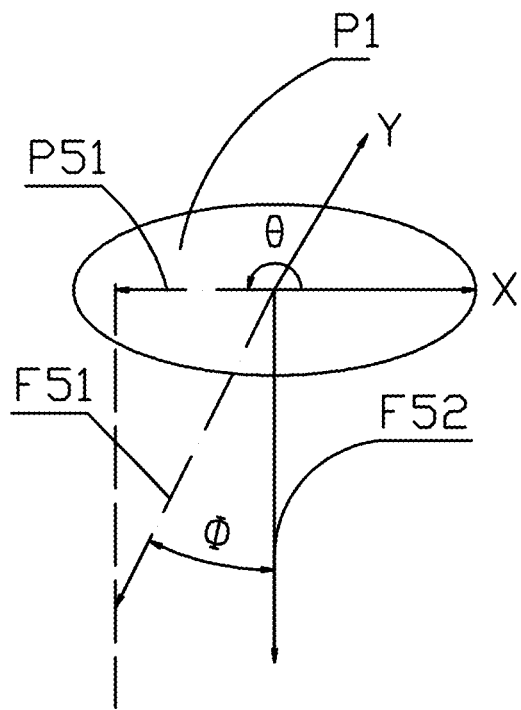
FIG. 6C schematically shows a technique for measuring the relative steering of the scanning body in FIG. 6B.

When performing three-dimensional ultrasound imaging, a two-dimensional array probe may be used, as shown in FIG. 6A. The two-dimensional array probe may include a plurality of transducers 112 which are arranged in transverse and longitudinal directions. Each transducer of the two-dimensional array probe may be provided with a delay control line, which may be used to control the time delay of the corresponding transducer. During the transmitting and the receiving of the ultrasound beam, the beam control and the dynamic focus of the ultrasound beam may be implemented by adjusting the time delay of each transducer, thereby changing the direction of the beam to implement the scanning of the beam in a three-dimensional space to obtain three-dimensional image data. As shown in FIG. 6B, the two-dimensional array probe 1 may include a plurality of transducers 112. By changing the time delay of the transducers used in current transmitting, the transmitted ultrasound beam may propagate in the direction indicated by the dot-chain arrow F51 and form a scanning body A1 (the three-dimensional structure drawn by the dot-chain lines in FIG. 6B) for obtaining three-dimensional image data in the three-dimensional space. The scanning body A1 may have a predetermined steering with respect to a reference body A2 (the three-dimensional structure drawn by the solid lines in FIG. 6B). The reference body A2 herein may be formed in the three-dimensional space by making the ultrasound beam transmitted by the used transducers to propagate in the normal direction of the plane on which the transducers are arranged (indicated by the solid-line arrow F52). Therefore, the steering of the scanning body A1 with respect to the reference body A2 may be used to measure the steered angle in a three-dimensional space of a scanning body formed by the propagation of an ultrasound beam in different directions with respect to a reference body. In the present disclosure, the steering may be measured by following two angles: the predetermined steered angle ϕ between the propagation direction of the ultrasound beam and the normal direction of the plane on which the transducers are arranged in the scanning plane A21 (the quadrilateral drawn by the dot-chain lines in FIG. 6B) of the ultrasound beam in the scanning body, which is in the range of [0, 90°), and the rotation angle θ formed by, in the plane rectangular coordinate system in the plane P1 on which the transducers are arranged, counterclockwise rotating X axis to the projection P51 (the dot-chain arrow in plane P1 in FIG. 6C) of the propagation direction of the ultrasound beam on the plane P1 on which the transducers are arranged, which is in the range of [0, 360°). In the case that the steered angle ϕ is zero, the steering of the scanning body A1 with respect to the reference body A2 is zero. During a three-dimensional ultrasound imaging, by changing the time delay of each transducer, the magnitude of the steered angle ϕ and the rotation angle θ may be changed to change the steering of the scanning body A1 with respect to the reference body A2, thereby forming different scanning bodies in different ultrasound propagation directions in the three-dimensional space.

The plane ultrasound beam generally almost covers the entire imaging area of the probe 1. In the case of performing ultrasound imaging using the plane ultrasound beam, one frame of ultrasound image (the one frame of ultrasound image herein should be understood as including one frame of two-dimensional image data or one frame of three-dimensional image data, and the same below) may be obtained by one transmission, therefore the imaging frame rate may be very high. While in the case of performing ultrasound imaging using the focused ultrasound beam, since the beam is focused at the focus, only one or several scan lines can be obtained by each transmission, therefore a plurality of transmissions need to be performed to obtain all scan lines within the imaging area so as to obtain one frame of ultrasound image of the imaging by combining all scan lines. Therefore, in the case of performing ultrasound imaging using the focused ultrasound beam, the frame rate is relatively low. However, the energy of the focused ultrasound beam is concentrated and the image data is only obtained at the energy concentrated location. Therefore the signal to noise ratio of the obtained echo signals is high and ultrasound images with better quality can be obtained.

In order to accurately track and display an actual velocity vector (described in detail below) of a target point (e.g., the point or location of interest in a scanning target) within a flow field of fluid (e.g., blood or other fluid within an organism, etc.) in the scanning target (e.g., blood vessel in the organ, tissue or the like of a human or animal, or other vessel of an organism in which fluid flows, etc.) in the ultrasound image, an ultrasound imaging method is provided by the present disclosure, in which the actual velocity vector of the target point within the flow field of the fluid in the scanning target can be accurately tracked by transmitting the ultrasound beams in a plurality of ultrasound propagation directions (described in detail below) and displayed in the ultrasound image. The ultrasound image herein may be a three-dimensional ultrasound image. Furthermore, the method also utilizes the advantage of the relatively high frame rates of the plane ultrasound beam imaging to satisfy the high frame rate requirement of the fluid velocity measurement using ultrasound imaging so as to obtain more accurate, real-time velocity vectors. Moreover, by transmitting the plane ultrasound beams in a plurality of ultrasound propagation directions, the obtained velocity vector of the target point is closer to the actual direction and magnitude of the velocity of the target point in the flow field in the scanning target, such that the real direction and magnitude of the velocity of the target point can be displayed in the three-dimensional image or two-dimensional image. The specific embodiments of the present disclosure will be described in detail below with reference to the drawings.

Figure 7:
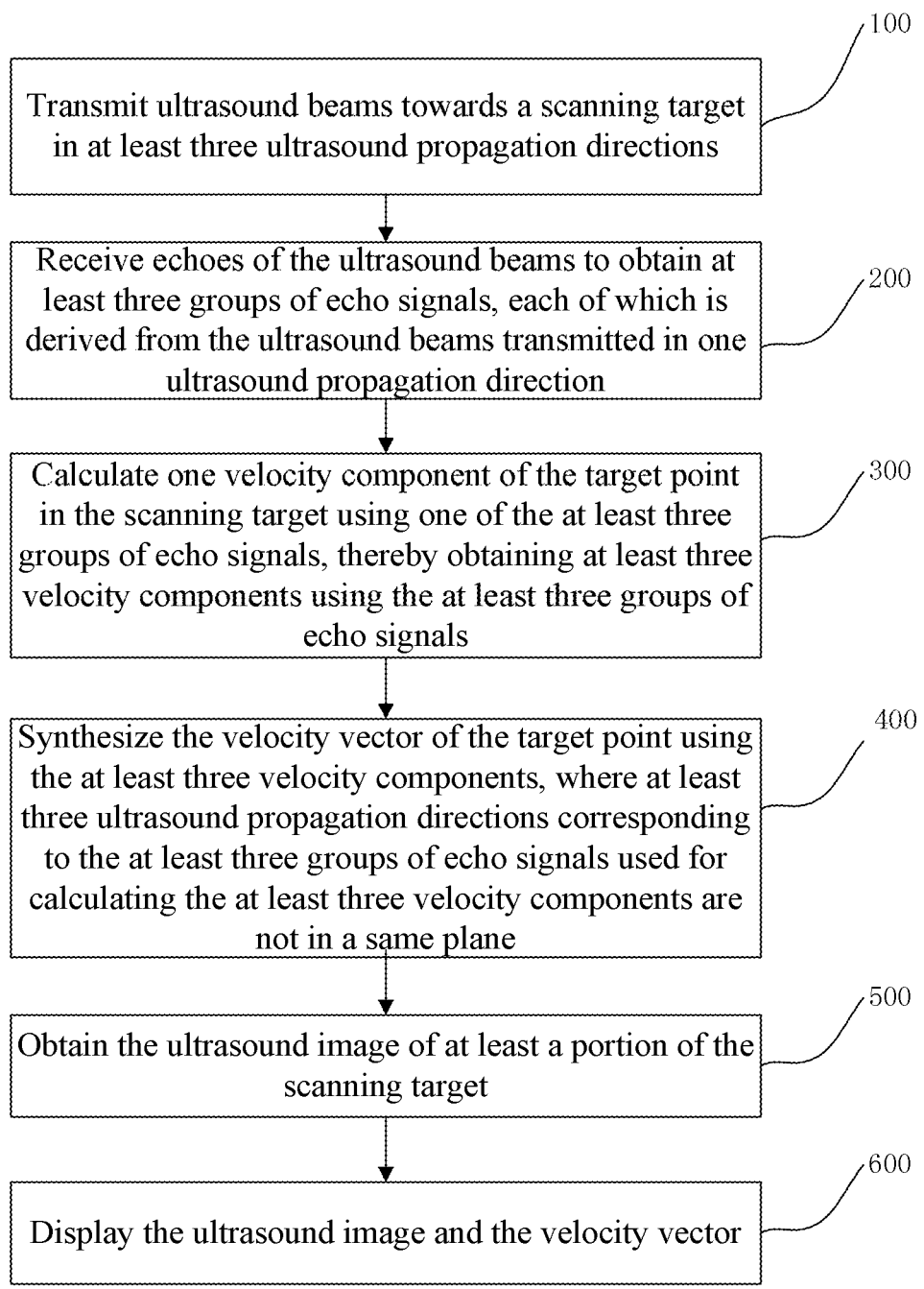
FIG. 7 is a flow chart corresponding to one embodiment.

As shown in FIG. 7, in one embodiment, an ultrasound imaging method is provided, which may include the following steps.

In step 100, the transmitting circuit 2 may excite the probe 1 to transmit ultrasound beams towards the scanning target in at least three ultrasound propagation directions. Each transducer of the probe 1 may be provided with a delay line, and the beam control and dynamic focus of the probe may be performed by adjusting the time delay of the transducers of the probe 1 so as to obtain different ultrasound propagation directions. The ultrasound beam herein may include any one of the plane ultrasound beam, the focused ultrasound beam and the diffusion ultrasound beam. In one embodiment, the transmitting circuit 2 may excite the probe 1 to transmit plane ultrasound beams towards the scanning target in at least three ultrasound propagation directions.

Figure 8:
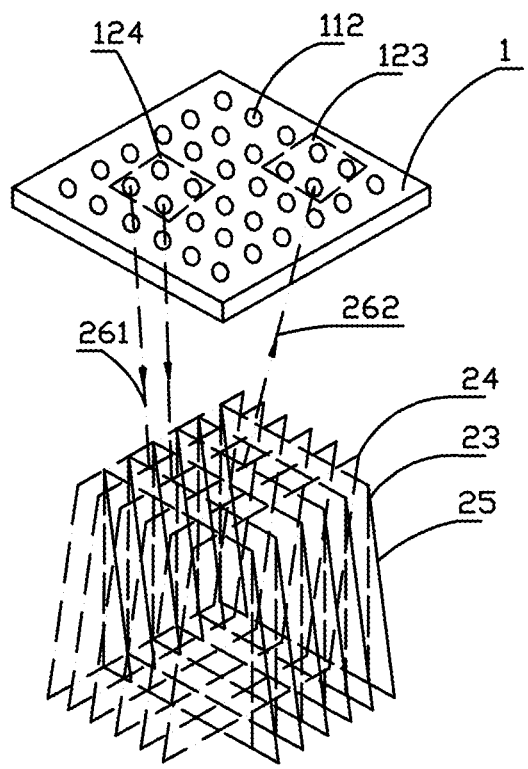
FIG. 8 schematically shows the spatial positions of the scanning planes in the scanning space in the ultrasound imaging method.
Figure 9:
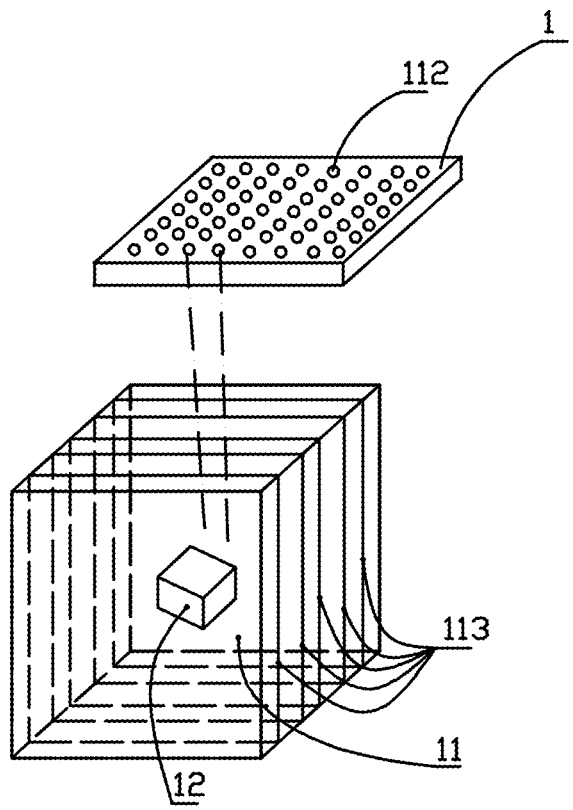
FIG. 9 schematically spatially shows forming a scanning body in one ultrasound propagation direction in FIG. 8.

As shown in FIG. 9 in which the transmitting of the plane ultrasound beam is taken as an example (but not limited to the plane ultrasound beam), when the transmitting circuit 2 excites the transducers 112 to be used in current transmitting to transmit plane ultrasound beams towards the scanning target 12 in one of the ultrasound propagation directions (such as the direction indicated by the dot-chain line in FIG. 9), a plurality of scanning planes 113 (represented by the solid line quadrilaterals 113 in FIG. 9) which are substantially parallel to each other may be formed during the propagation of the ultrasound beam in the space in which the scanning target 12 is located. The plurality of scanning planes 113 may form a scanning body 11. A frame of plane beam echo image data may be obtained by receiving the echoes from the scanning body 11 to obtain ultrasound beam echo signals and processing the ultrasound beam echo signals, which may be used to form a three-dimensional image database. The one frame of plane beam echo image data may include one frame of three-dimensional image data, or may also be considered as one frame of three-dimensional image data formed by a plurality of two-dimensional image data. Another example is shown in FIG. 8, which schematically shows the formation of three scanning bodies in three ultrasound propagation directions according to the process shown in FIG. 9. In FIG. 8, the transmitting circuit 2 may excite the transducers 4 of the probe 1 to be used in current transmitting to transmit ultrasound beams towards the scanning target in three ultrasound propagation directions. Three groups of substantially parallel scanning planes 24, 23, 25 may be formed during the propagation of the ultrasound beams in the space in which the scanning target is located. The three groups of substantially parallel scanning planes 24, 23, 25 may form three scanning bodies, respectively. Three groups of plane beam echo image data may be obtained by receiving the echoes from the three scanning bodies to obtain three groups of ultrasound beam echo signals and processing the three groups of ultrasound beam echo signals, which may be used to obtain three groups of three-dimensional image data acquired at the same time. The velocity vector of the target point in the scanning target may be calculated based on the three groups of three-dimensional image data. In FIG. 8, the transducers used in the transmitting of the ultrasound waves may be a part or all of the transducers of the probe 1, and the transducers used in the receiving of the echoes may also be a part or all of the transducers of the probe 1. In FIG. 8, the part of transducers 124 may be used to transmit the ultrasound beams in the ultrasound propagation direction 261, and the part of transducers 123 may be used to receive the echoes of the ultrasound waves in the direction 262.

Figure 10:
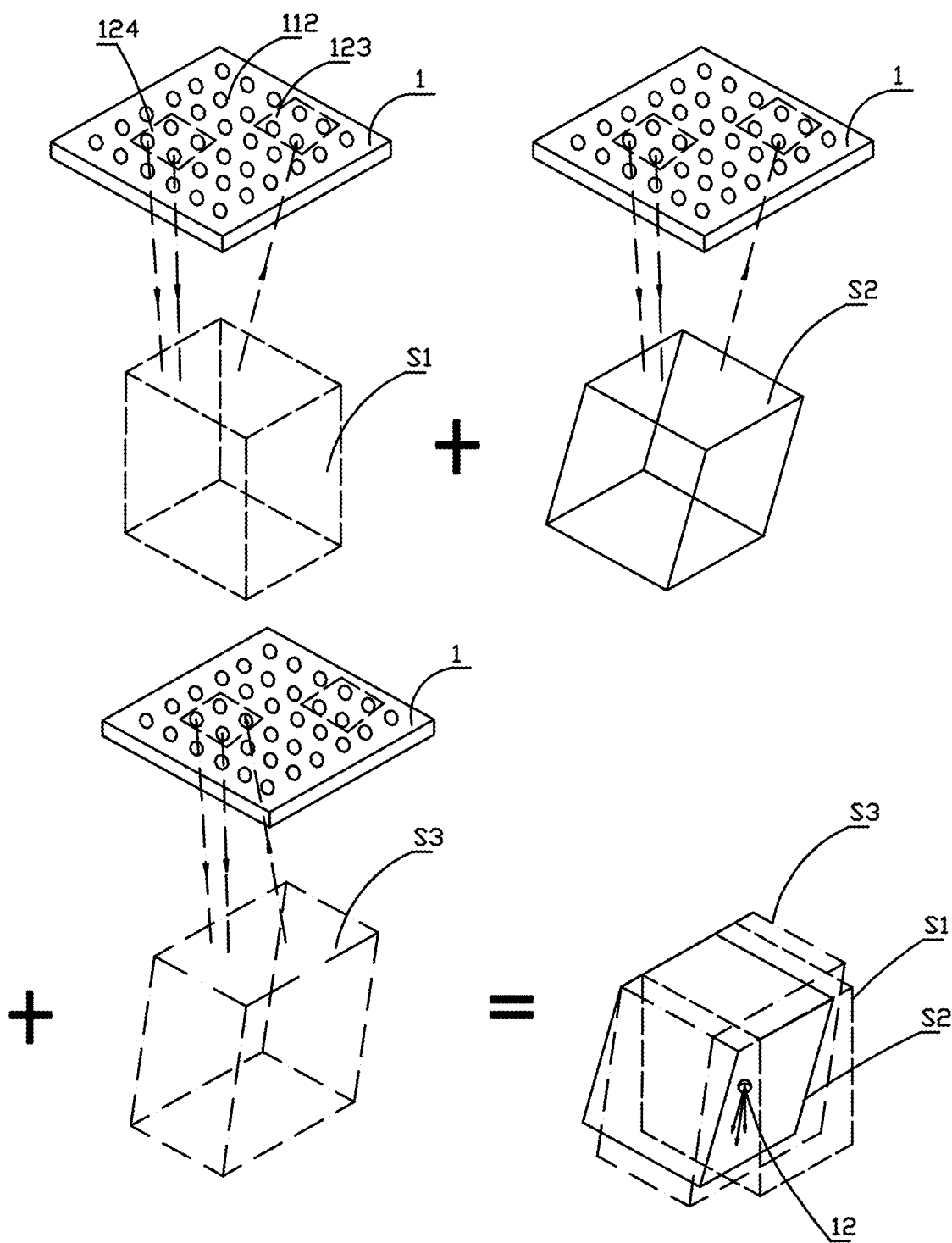
FIG. 10 schematically shows the spatial superposition effect of the three scanning bodies formed in three ultrasound propagation directions.

In one embodiment, in step 100, a part or all of the transducers may be excited to transmit ultrasound beams towards the scanning target in at least three ultrasound propagation directions, such that the ultrasound beams may propagate in the space in which the scanning target is located to form at least three scanning bodies. Each scanning body may be derived from the ultrasound beams transmitted in one ultrasound propagation direction. As shown in FIG. 10, a part or all of the transducers of the probe 1 may be respectively excited to transmit ultrasound beams towards the scanning target in three ultrasound propagation directions to form three scanning bodies S1, S2, S3. The data where the echo signals from the three scanning bodies S1, S2, S3 overlap may be used to calculate the velocity vector of the target point within the scanning target 12. There may be steering between any two of the plurality of scanning bodies, and the plurality of scanning bodies may at least partially overlap. Based on the embodiment above, in another embodiment, in step 100, a part or all of the transducers may be excited to transmit plane ultrasound beams towards the scanning target in at least three ultrasound propagation directions such that the plane ultrasound beams propagate in the space in which the scanning target is located to form at least three scanning bodies. Each scanning body may be derived from the plane ultrasound beams transmitted in one ultrasound propagation direction. Of course, the present disclosure is not limited to the plane ultrasound beams. The diffusion ultrasound beams or the focused ultrasound beams may also be used. Furthermore, the part or all of the transducers used in the transmitting may be a part or all of the transducers of the probe 1, or a part or all of the transducers arranged in a plane in the probe 1. For example, the part or all of the transducers mentioned above may be the transducers within a rectangular area (such as 124 in FIG. 10 and FIG. 8) in a two-dimensional array probe, the transducers in at least one circle or transducers within at least one fan-shape area (such as 111 in FIG. 11C) in a ring two-dimensional array probe, etc. It may also be understood as that the part or all of the transducers mentioned above may be a part or all of the transducers within a rectangular area in a rectangular two-dimensional array probe or a part or all of the transducers in at least one circle or within at least one fan-shape area in a ring two-dimensional array probe. The part or all of the transducers mentioned below will be understood similarly.

Figure 11A:
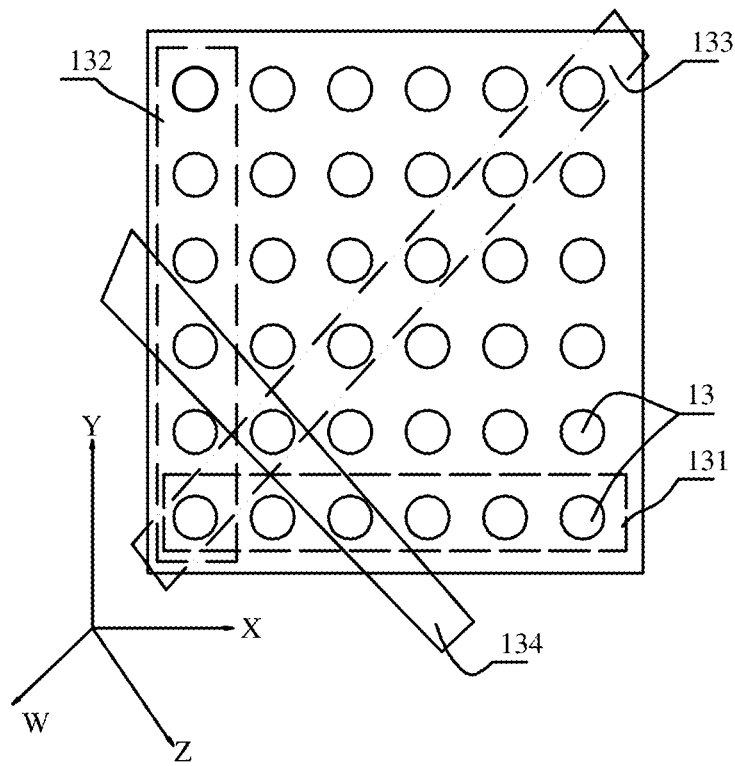
FIG. 11A schematically shows the relation between the transducer arrangement and the transducer positions of the two-dimensional array probe.
Figure 11B:
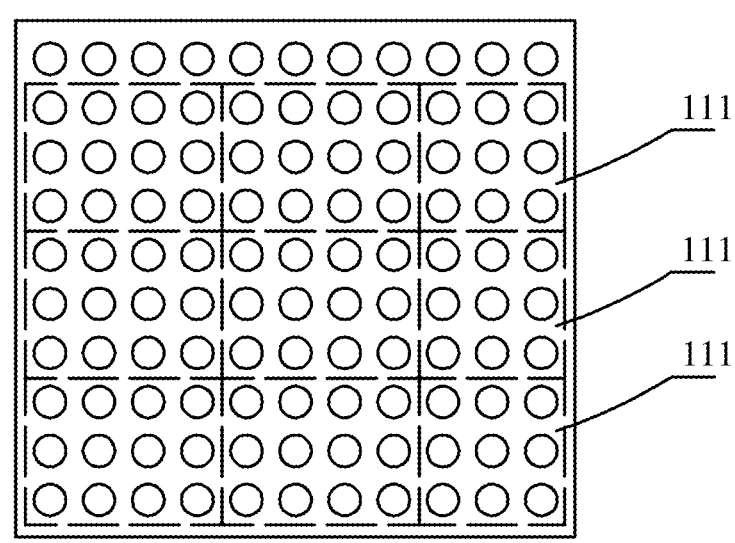
FIG. 11B schematically shows the divided transducer regions of the two-dimensional array probe.
Figure 12:
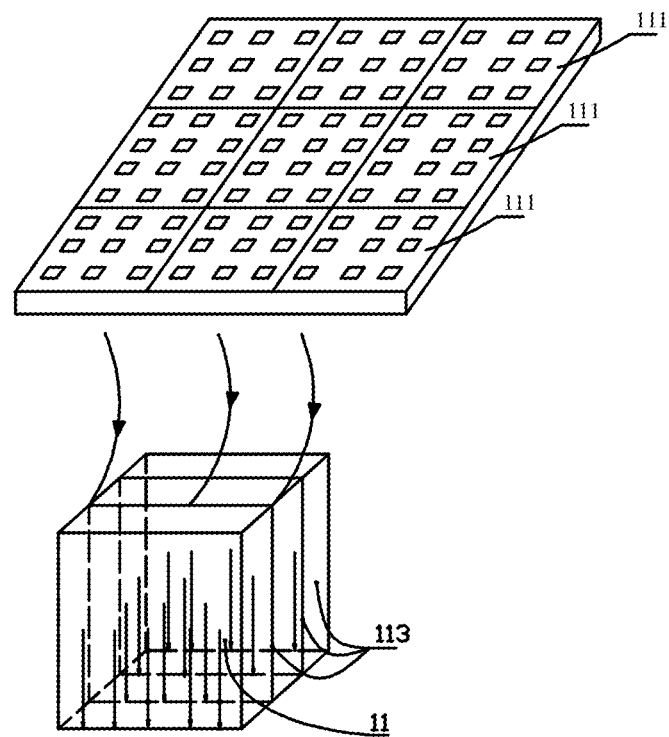
FIG. 12 schematically shows the spatial positions of the scanning bodies obtained by the transducer regions.

In addition, in another embodiment, as shown in FIG. 11B, the ultrasound wave transmitting transducer (one circle represents one transducer in the figure) of the probe 1 may be divided into a plurality of transducer regions 111. A part or all of the transducer regions 111 may be excited to transmit ultrasound beams towards the scanning target in at least three ultrasound propagation directions such that the ultrasound beams may propagate in the space in which the scanning target is located to form at least three scanning bodies. Each transducer region 111 has a predetermined delay control mode used to control the transmitting time delay of the ultrasound beams transmitted by the part or all of the ultrasound wave transmitting transducer. In this case, a part or all of the transducer regions 111 may be used to receive the ultrasound echoes, or, a part or all of the ultrasound wave transmitting transducers of the transducer region 111 may be used to receive the ultrasound echoes. This embodiment may be suitable for, but not limited to, the transmitting of the focused ultrasound beam. As shown in FIG. 12, taking the transmitting of the focused ultrasound beam as an example, each transducer region 111 may be used to generate at least one focused ultrasound beam (e.g., the arcs with arrow in the figure). Therefore, when a plurality of transducer regions 111 are excited at the same time to generate focused ultrasound beams, a plurality of focused ultrasound beams may propagate in the space in which the scanning target is located to form a scanning body 11 formed by the focused ultrasound beams. The focused ultrasound beams in a same plane within the scanning body 11 may form a scanning plane 113 (as shown by the solid arrows in the figure and each solid arrow may represent one focused ultrasound beam). The scanning body 11 may also be considered as being formed by a plurality of scanning plane 113. By changing the time delay of the transmitting transducers used in the current transmitting in each transducer region 111, the direction of the focused ultrasound beam may be changed, and thereby the propagation direction of the plurality of focused ultrasound beams in the space in which the scanning target is located may be changed. Therefore, in another embodiment, the ultrasound wave transmitting transducers of the probe 1 may be divided into a plurality of transducer regions, and a part or all of the transducer regions may be excited to transmit focused ultrasound beams towards the scanning target in at least three ultrasound propagation directions such that the focused ultrasound beams propagate in the space in which the scanning target is located to form at least three scanning bodies. Each transducer region may generate at least one focused ultrasound beam.

Figure 11C:
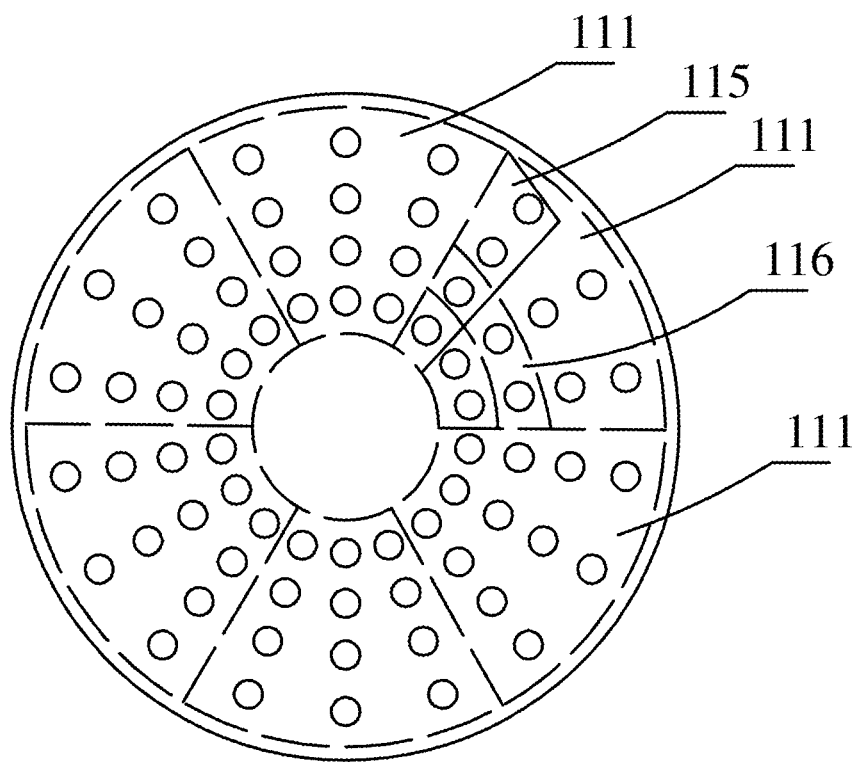
FIG. 11C schematically shows the divided transducer regions of a ring array probe.
Figure 11D:
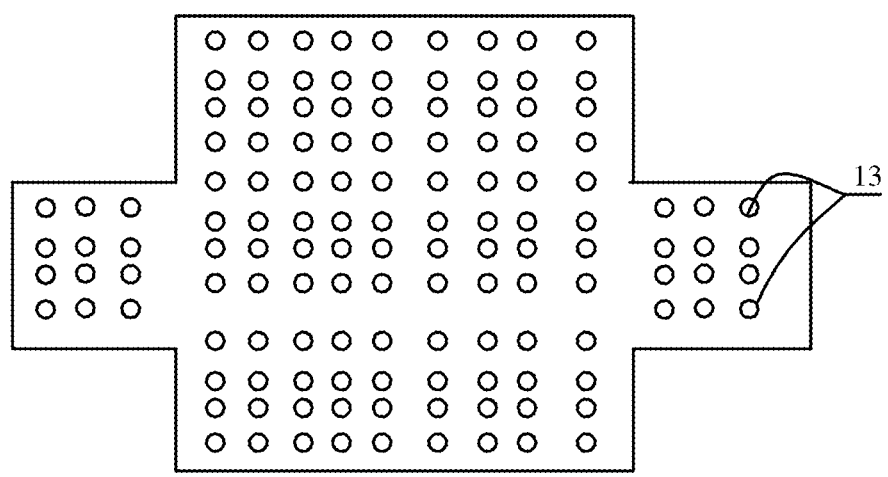
FIG. 11D schematically shows a probe in which the transducers are arranged irregularly.

Based on the embodiments above, besides the rectangle two-dimensional array probe, a ring two-dimensional array probe as shown in FIG. 11C may also be used. Therefore, the plurality of transducer regions mentioned above may be evenly divided in transverse and longitudinal directions of the two-dimensional array probe as shown in FIG. 11B, or be evenly divided into a plurality of fan-shaped regions as the transducer regions 111 mentioned above in circumference direction. Similarly, the probes mentioned herein are not limited to those described above. Rather, the two-dimensional array probe formed by a plurality of transducers arranged irregularly may also be used. The dividing of the transducer regions 111 may refer to the manners shown in FIG. 11, such as evenly dividing the transducers into a plurality of fan-shaped regions in the arrangement direction of the transducers or the circumference direction, or dividing the transducers into a plurality of concentric rings as the transducer regions in the radial direction, or dividing the transducers into a plurality of block-like transducer regions with arbitrary shape, etc. In one embodiment, in the abnormal arrangement of the ultrasound transducers 13 shown in FIG. 11D, the transducers of the probe 1 may be arranged as a plane with arbitrary shape, and the transducer regions 111 thereof may be block-like transducer regions with arbitrary shape including at least one transducer.

The ultrasound beams in at least three propagation directions transmitted in step 100 may be used to provide basic data for the calculation in step 400. The ultrasound echoes in one ultrasound propagation direction may be used to calculate one velocity component of the target point in the one ultrasound propagation direction. In order to make the velocity vector of the target point obtained by the present disclosure to be more coincident with the actual situation and more realistically represent the actual blood flow velocity of the blood flow at the target point, in step 400 of the present embodiment, the echoes of the ultrasound beams transmitted in at least three ultrasound propagation directions may be used to calculate the velocity vector of the target point. Specifically, in step 400, when calculating the velocity vector of the target point using at least three velocity components, the following constraint about the ultrasound propagation direction may be satisfied: the at least three ultrasound propagation directions corresponding to the at least three groups of echo signals used to calculate the at least three velocity components are not in a same plane.

Figure 13:
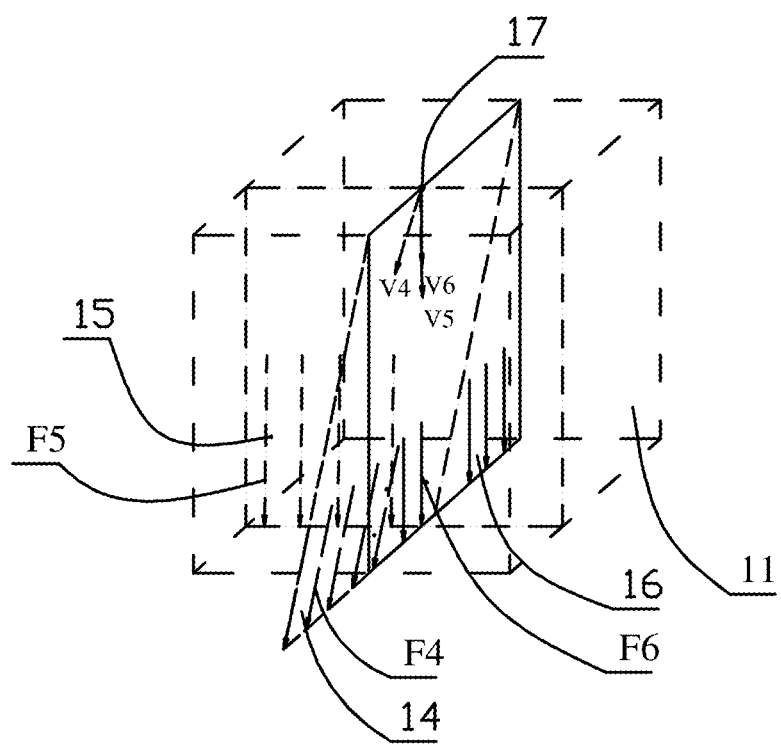
FIG. 13 schematically shows the positions of the scanning implemented in three ultrasound propagation directions.

The embodiments of FIG. 13 to FIG. 18 schematically show only one scanning plane in the scanning body formed in one ultrasound propagation direction in order to more clearly show the difference between the scanning bodies formed in different ultrasound propagation directions. As shown in FIG. 13, when the ultrasound beams are transmitted towards the scanning target in one of the ultrasound propagation directions (such as the direction of the solid arrow F6 in FIG. 13), the ultrasound beams may propagate in a scanning section of the scanning space in which the scanning target is located to form the scanning plane 16 (i.e., the solid line quadrilateral 16 in FIG. 13). The echo signals of the ultrasound beams may be obtained and processed to obtain one frame of plane beam echo image data which may be used to form a two-dimensional image data of the section. A plurality of substantially parallel scanning planes 16 may form the scanning body 11 (the dotted line cube in the figure). The image data of a plurality of sections may be obtained by obtaining and processing all echo signals of the scanning body 11 and used to form the three-dimensional image data. Three scanning plane formed in the case of scanning the scanning space in three ultrasound propagation directions are shown in FIG. 13, in which the scanning plane 16 is formed by transmitting one plane ultrasound beam towards the scanning target in the ultrasound propagation direction represented by the solid arrow F6, the scanning plane 15 is formed by transmitting one plane ultrasound beam towards the scanning target in the ultrasound propagation direction represented by the double-dotted line arrow F5, and the scanning plane 14 is formed by transmitting one plane ultrasound beam towards the scanning target in the ultrasound propagation direction represented by the dotted arrow F4. In FIG. 13, the scanning plane 15 and the scanning plane 16 may be perpendicular to each other, and their propagation directions may both be the depth direction of the scanning space 11. Therefore, the scanning bodies formed by a plurality of substantially parallel scanning planes 15 and scanning planes 16 may both be within the cube represented by the dashed line, and cover the same scanning range. Thus, when a part or all of the ultrasound wave transmitting transducers at a same location, or a same transducer region or all transducer regions, of the probe are used to form the scanning plane 15 and the scanning plane 16, it may be considered that they have the same ultrasound propagation direction. However, the ultrasound propagation direction of the scanning plane 14 may be different from that of the scanning plane 15 and the scanning plane 16. Hence, in one embodiment, in step 100, the transmitting circuit 2 may excite the probe 1 to transmit ultrasound beams towards the scanning target in at least three ultrasound propagation directions such that the propagation of the ultrasound beams in the space in which the scanning target is located may form at least three scanning bodies which may at least partially overlap in space.

In step 100, the ultrasound beams may also be transmitted towards the scanning target in N (3≤N) ultrasound propagation directions, and in subsequent step 400, only n velocity components are used to calculate the velocity vector of the target point, where 3≤n<N. In other words, in step 100, ultrasound beams may be transmitted towards the scanning target in at least three ultrasound propagation directions which are not in a same plane, and in step 400, the velocity components of the target point in at least three of the ultrasound propagation directions corresponding to the at least three groups of echo signals received may be calculated respectively based on the fact that each one of the at least three groups of echo signals may be used to calculate one velocity component of the target point in the scanning target, and the velocity vector of the target point may be synthesized based on the velocity components in the at least three of the ultrasound propagation directions.

As another example, in order to decrease the calculation and reduce the complexity of the scanning and calculation, in step 100, the ultrasound beams may be transmitted towards the scanning target in N (3≤N) ultrasound propagation directions, and in subsequent step 400, N velocity components may be used to calculate the velocity vector of the target point. In other words, in step 100, ultrasound beams may be transmitted towards the scanning target in at least three ultrasound propagation directions which are not in a same plane, and in step 400, the velocity components of the target point in all of the ultrasound propagation directions corresponding to the at least three groups of echo signals received may be calculated respectively based on the fact that each one of the at least three groups of echo signals may be used to calculate one velocity component of the target point in the scanning target, and the velocity vector of the target point may be synthesized based on the velocity components in all of the ultrasound propagation directions.

In order to satisfy the constraint about the ultrasound propagation direction, either "adjacent at least three ultrasound propagation directions being not in a same plane" or "the at least three ultrasound propagation directions being not in a same plane" may be satisfied by obtaining different ultrasound propagation directions by adjusting the time delay of the transducers used in the transmission of the ultrasound beams and/or driving the transducers used in the transmission of the ultrasound beams to swing to change the exiting direction of the ultrasound beams. Driving the transducers used in the transmission of the ultrasound beams to swing to change the exiting direction of the ultrasound beams may be implemented by, for example, providing a mechanical drive control unit for the transmitting transducers which may be used to drive the transmitting transducers to swing a pre-set angle such that the exiting direction of the ultrasound beam may have a pre-set steered angle with respect to the normal of the transducer arrangement plane.

Figure 15:
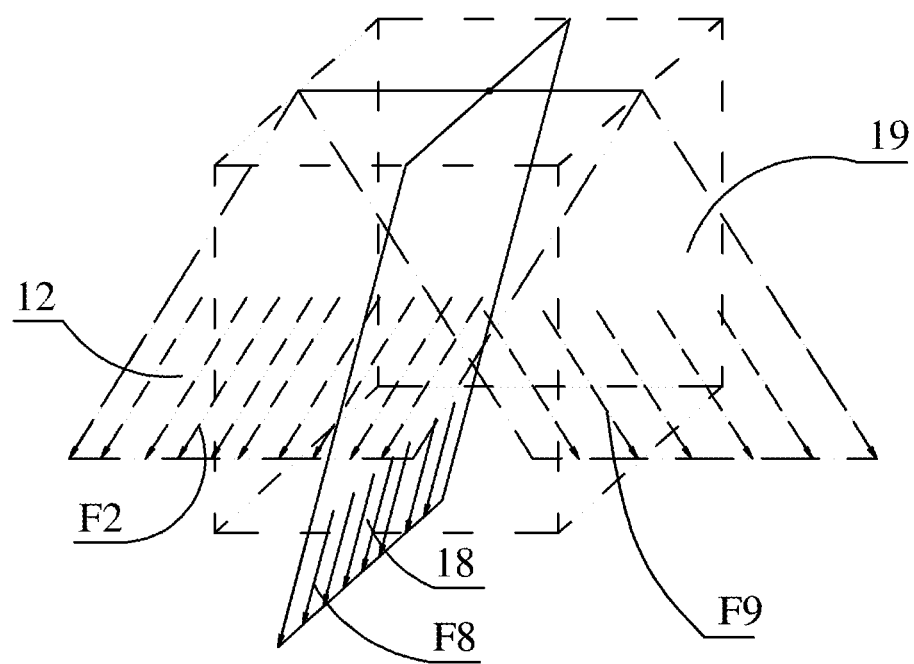
FIG. 15 schematically shows the positions of the scanning implemented in three ultrasound propagation directions.
Figure 17:
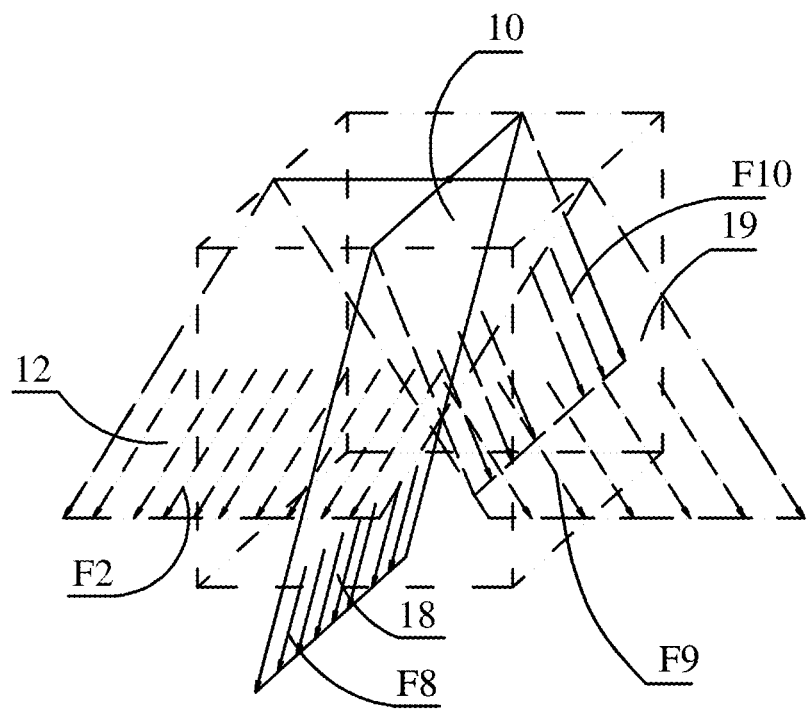
FIG. 17 schematically shows the positions of the scanning implemented in four ultrasound propagation directions.
Figure 18:
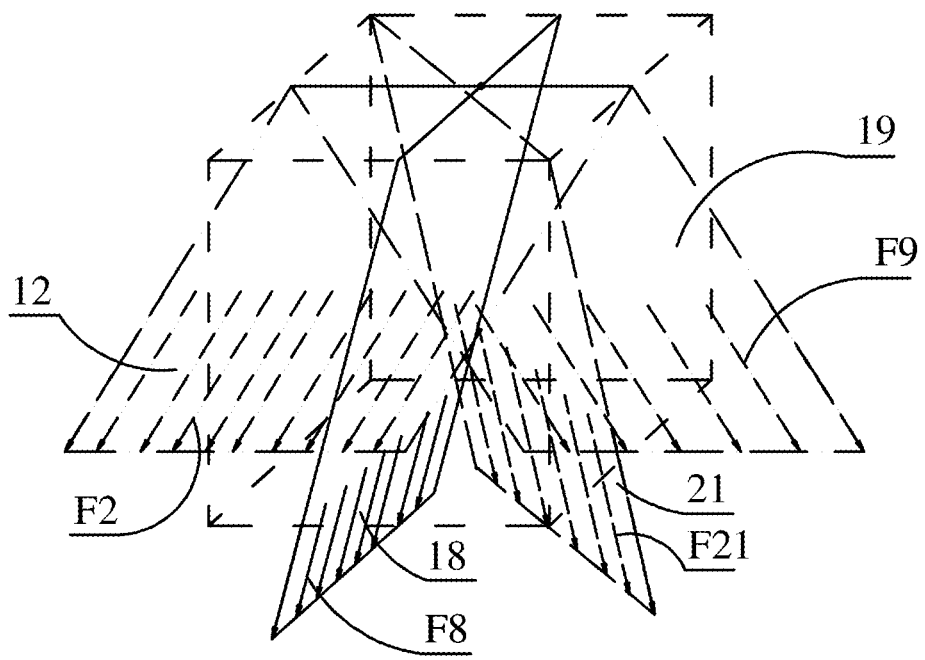
FIG. 18 schematically shows the positions in one embodiment in which the scanning in four ultrasound propagation directions is implemented.

In order to reduce the complexity of subsequent calculation and facilitate the compensation to the echo signals in subsequent calculation, the ultrasound propagation directions above may have space symmetry. It may also be understood as that, when transmitting ultrasound beams towards the scanning target in different ultrasound propagation directions, at least two of the ultrasound propagation directions are symmetrical with respect to the normal of the transducer arrangement plane and/or to a plane perpendicular to the transducer arrangement plane. For example, the steered angles φ of the resultant ultrasound beams in the two symmetrical ultrasound propagation directions are equal, or, the projections of the two ultrasound propagation directions in the transducer arrangement plane are symmetrical with respect to any straight line passing through the origin of a plane rectangular coordinate system in the transducer arrangement plane. For example, the difference (or the absolute value of the difference) between the rotation angles θ of the resultant ultrasound beams may be 180 degree. The definition of the steered angle φ and the rotation angle θ may refer to those described above, and the same below. Three scanning bodies formed in the case of scanning the scanning space in three ultrasound propagation directions are shown in FIG. 15, in which the scanning plane of the scanning body formed by transmitting one plane ultrasound beam towards the scanning target in the ultrasound propagation direction F8 represented by the solid arrow may be represented by the solid line quadrilateral 18, the scanning plane of the scanning body formed by transmitting one plane ultrasound beam towards the scanning target in the ultrasound propagation direction F9 represented by the single-dotted line arrow may be represented by the single-dotted line quadrilateral 19, and the scanning plane of the scanning body formed by transmitting one plane ultrasound beam towards the scanning target in the ultrasound propagation direction F2 represented by the double-dotted line arrow may be represented by the double-dotted line quadrilateral 12. As shown in FIG. 15, the ultrasound propagation directions F2 and F9 are symmetrical with respect to the normal of the transducer arrangement plane or to the plane perpendicular to the transducer arrangement plane. Specifically, it may be understood as that the resultant ultrasound beams in the symmetrical ultrasound propagation directions may have the same steered angle φ and the difference (or the absolute value of the difference) between their rotation angles θ may be 180 degree. FIG. 17 schematically shows four scanning bodies formed in the case of scanning the scanning space in four ultrasound propagation directions, which may be formed by addition to FIG. 15. The scanning plane of the scanning body formed by transmitting one ultrasound beam towards the scanning target in the ultrasound propagation direction F10 represented by the dashed line arrow may be represented by the dashed line quadrilateral 10. As shown in FIG. 17, the ultrasound propagation directions F2 and F9, and F8 and F10, are symmetrical with respect to the normal of the transducer arrangement plane. It may be understood as that the resultant ultrasound beams in the symmetrical ultrasound propagation directions F2 and F9, and F8 and F10, may have the same steered angle φ and the difference (or the absolute value of the difference) between their rotation angle θ may be 180 degree. FIG. 18 schematically shows four scanning bodies formed in the case of scanning the scanning space in four ultrasound propagation directions, which may be formed by addition to FIG. 15. The scanning plane of the scanning body formed by transmitting one ultrasound beam towards the scanning target in the ultrasound propagation direction F21 represented by the dashed line arrow may be represented by the dashed line quadrilateral 21. The ultrasound propagation directions F2 and F9 are symmetrical with respect to the normal of the transducer arrangement plane, and F8 and F10 are symmetrical with respect to the plane perpendicular to the transducer arrangement plane, which may be understood as that the resultant ultrasound beams in the two symmetrical ultrasound propagation directions F8 and F21 may have the same steered angle φ and the projections of F8 and F21 in the transducer arrangement plane may be symmetrical with respect to any straight line passing through the origin of the plane rectangular coordinate system. It can be seen from the embodiments above that, in one embodiment, each pair of ultrasound propagation directions may be symmetrical with respect to the normal of the transducer arrangement plane and/or to the plane perpendicular to the transducer arrangement plane.

As another example, in another embodiment, in the case that the number of the ultrasound propagation directions is even, the ultrasound propagation directions may be located in a rotating surface whose central axis is the normal of the transducer arrangement plane, and the ultrasound propagation directions may be symmetrical in pairs with respect to the central axis, as shown in FIG. 18. In one embodiment, in step 100, the transmitting circuit 2 may excite the probe 1 to transmit ultrasound beams towards the scanning target in four ultrasound propagation directions which are symmetrical in pairs with respect to the plane perpendicular to the transducer arrangement plane, as shown in FIG. 18. It may also be understood as that, in one embodiment, the resultant ultrasound beams in different ultrasound propagation direction may have the same steered angle φ, and the projections of these ultrasound propagation directions in the transducer arrangement plane may be symmetrical in pairs with respect to any straight line passing through the origin of the plane rectangular coordinate system. For example, the difference (or the absolute value of the difference) between the rotation angles θ of the two may be 180 degree. In another embodiment, as shown in FIG. 15, in step 100, the transmitting circuit 2 may excite the probe 1 to transmit ultrasound beams towards the scanning target in three ultrasound propagation directions, and the angle between any two of the three ultrasound propagation directions may be 60 degree.

In addition, FIG. 11A schematically shows the two-dimensional array probe in which a plurality of transducers are arranged in array or the transmitting transducer region 124 in which a plurality of transducers are arranged in array. The two-dimensional array probe of the transmitting transducer region 124 may be considered as being formed by a plurality of linear array transducer groups, and the linear array transducers may be considered as being arranged in a plurality of directions. For example, in the figure, the two-dimensional array probe or the transmitting transducer region 124 may be considered as being formed by a plurality of linear array transducer groups 131 arranged in Y direction, or being formed by a plurality of linear array transducer groups 132 arranged in X direction, or being formed by a plurality of linear array transducer groups 133 arranged in Z direction, or being formed by a plurality of linear array transducer groups 134 arranged in W direction, etc.

Therefore, in order to simplify the control scheme of the delay lines, in one embodiment, exciting a part or all of the ultrasound wave transmitting transducers to transmit ultrasound beams towards the scanning target in at least three ultrasound propagation directions may be implemented using various techniques.

Figure 16:
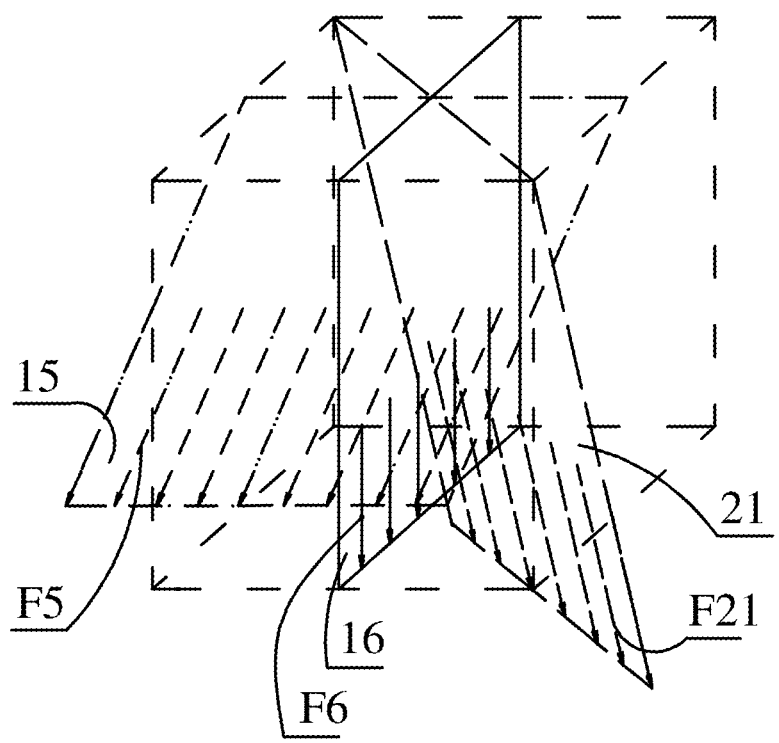
FIG. 16 schematically shows the positions of the scanning implemented in three ultrasound propagation directions.

The first technique may be performing delay control on the plurality of linear array transducer groups of the part or all of the ultrasound wave transmitting transducers in at least three direction, respectively, such that the plurality of linear array transducer groups are excited in one direction and are respectively successively excited in at least two directions to transmit ultrasound beams, and thereby the ultrasound beams may propagate in the space in which the scanning target is located in at least three ultrasound propagation directions to form at least three scanning bodies, respectively. When the plurality of linear array transducer groups are successively excited in a same direction to transmit the ultrasound beams, one scanning body may be formed. In this case, the transducers of each group of linear array transducers may be excited at the same time. FIG. 16 schematically shows three scanning bodies formed by scanning the scanning space in three ultrasound propagation directions. The delay control may be performed on the plurality of linear array transducer groups 132 in the X direction such that the plurality of linear array transducer groups 132 may be successively excited in the Y direction to transmit ultrasound beams in the ultrasound propagation direction F5 represented by the double-dotted line arrow, and the scanning plane in the scanning body formed by the propagation of the ultrasound beams in the three-dimensional space may be represented by the double-dotted line quadrilateral 15. The delay control may be performed on the plurality of linear array transducer groups 131 in the Y direction such that the plurality of linear array transducer groups 131 may be simultaneously excited in the X direction to transmit ultrasound beams in the ultrasound propagation direction F6 represented by the solid arrow, i.e., the time delay in the X direction may be zero, and the scanning plane in the scanning body formed by the propagation of the ultrasound beams in the three-dimensional space may be represented by the solid line quadrilateral 16. The delay control may be performed on the plurality of linear array transducer groups 133 in the Z direction such that the plurality of linear array transducer groups 133 may be successively excited in the Z direction to transmit ultrasound beams in the ultrasound propagation direction F21 represented by the dashed line arrow, and the scanning plane in the scanning body formed by the propagation of the ultrasound beams in the three-dimensional space may be represented by the dashed line quadrilateral 21.

The second technique may be performing delay control on the plurality of linear array transducer groups of the part or all of the ultrasound wave transmitting transducers in at least three direction, respectively, such that the plurality of linear array transducer groups are respectively successively excited in at least three directions to transmit ultrasound beams, and thereby the ultrasound beams may propagate in the space in which the scanning target is located in at least three ultrasound propagation directions to form at least three scanning bodies, respectively. When the plurality of linear array transducer groups are successively excited in a same direction to transmit the ultrasound beams, one scanning body may be formed. In this case, the transducers of each group of linear array transducers may be excited at the same time. As shown in FIG. 16, the solid line quadrilateral 16 in FIG. 16 may be replaced by the solid line quadrilateral 18 in FIG. 18, i.e., the delay control may be performed on the plurality of linear array transducer groups 131 in the Y direction such that the plurality of linear array transducer groups 131 may be excited successively in the Y direction to transmit ultrasound beams in the ultrasound propagation direction F8 represented by the solid arrow, and the scanning plane in the scanning body formed by the propagation of the ultrasound beams in the three-dimensional space may be represented by the solid line quadrilateral 18. Actually, the first technique may be a special case of the second technique, in which a delay control strategy of zero time delay is provided to the plurality of linear array transducer groups of the part or all of the ultrasound wave transmitting transducers in one direction.

As another example, in one embodiment, in the first technique and the second technique above, when performing the delay control on the plurality of linear array transducer groups of the part or all of the ultrasound wave transmitting transducers in each direction, a same delay control strategy may be used, and each time the delay control strategy may be performed on the plurality of linear array transducers in pre-set time interval in order to excite them successively, such that the resultant ultrasound beams in the scanning body have predetermined steered angle φ and rotation angle θ. Alternatively, when performing the delay control on the plurality of linear array transducer groups of the part or all of the ultrasound wave transmitting transducers in each direction, more than one delay control strategies may be used. Therefore, when the delay control is performed on the plurality of linear array transducer groups of the part or all of the ultrasound wave transmitting transducer according one delay control strategy in one direction, a corresponding scanning body may be formed by the propagation of the ultrasound beams in one ultrasound propagation direction, and the resultant ultrasound beams in the scanning body may have predetermined steered angle φ and rotation angle θ. Hence, in order to have the ability of performing three-dimensional scanning on the scanning target in more ultrasound propagation directions using the same probe 1, in one embodiment, the delay control may be performed on the plurality of linear array transducer groups of the part or all of the ultrasound wave transmitting transducers according to at least one delay control strategy in each direction. For example, FIG. 18 schematically shows four scanning bodies formed by scanning the scanning space in four ultrasound propagation directions. A certain delay control may be performed on the plurality of linear array transducer groups 131 in the Y direction such that the plurality of linear array transducer groups 131 may be successively excited in the Y direction to transmit ultrasound beams in the ultrasound propagation direction F8 represented by the solid arrow, and the scanning plane in the scanning body formed by the propagation of the ultrasound beams in the three-dimensional space may be represented by the solid line quadrilateral 18. A delay control may be performed on the plurality of linear array transducer groups 132 in the X direction according to a first delay control strategy such that the plurality of linear array transducer groups 132 may be successively excited in the X direction to transmit ultrasound beams in the ultrasound propagation direction F2 represented by the double-dotted line arrow, and the scanning plane in the scanning body formed by the propagation of the ultrasound beams in the three-dimensional space may be represented by the double-dotted line quadrilateral 12. The resultant ultrasound beams in the double-dotted line quadrilateral 12 may have steered angle φ of X1 degree and corresponding rotation angle φ of 180 degree. A delay control may be performed on the plurality of linear array transducer groups 132 in the X direction according to a second delay control strategy such that the plurality of linear array transducer groups 132 may be successively excited in the X direction to transmit ultrasound beams in the ultrasound propagation direction F9 represented by the single-dotted line arrow, and the scanning plane in the scanning body formed by the propagation of the ultrasound beams in the three-dimensional space may be represented by the single-dotted line quadrilateral 19. The resultant ultrasound beams in the single-dotted line quadrilateral 19 may have steered angle φ of X1 degree and corresponding rotation angle φ of 0 degree. Of course, the steered angle φ may also not equal to X1. A certain delay control may be performed on the plurality of linear array transducer groups 133 in the Z direction such that the plurality of linear array transducer groups 133 may be successively excited in the Z direction to transmit ultrasound beams in the ultrasound propagation direction F21 represented by the dashed line arrow, and the scanning plane in the scanning body formed by the propagation of the ultrasound beams in the three-dimensional space may be represented by the dashed line quadrilateral 21.

Figure 14:
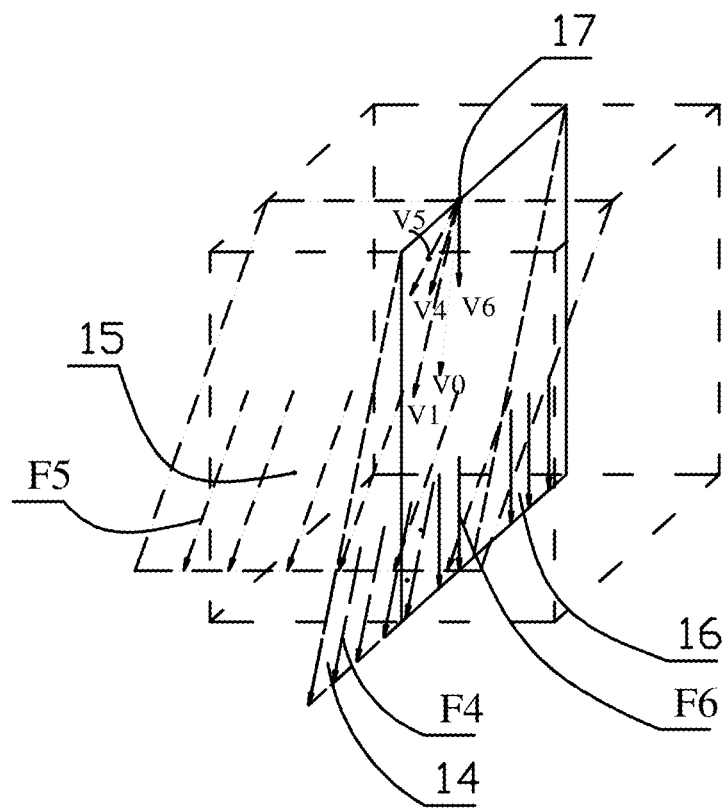
FIG. 14 schematically shows the positions of the scanning implemented in three ultrasound propagation directions.

In addition, in order to optimize the excitation scheme of the transducer of the probe to facilitate the excitation operation thereof and simplify the operation of the delay lines of the probe, in one embodiment, a third technique may be provided. For example, delay control may be performed on the plurality of linear array transducer groups of the part or all of the ultrasound wave transmitting transducers in two direction, respectively. In at least one direction, the delay control may be performed according to at least two delay control strategies. Thereby, the plurality of linear array transducer groups may be successively excited based on corresponding delay control strategies in each direction to transmit the ultrasound beams which will propagate in the space in which the scanning target is located in an ultrasound propagation direction to form a scanning body. In this case, the transducers of each group of linear array transducers may be excited at the same time. FIG. 14 schematically shows three scanning bodies formed by scanning the scanning space in three ultrasound propagation directions. A delay control may be performed on the plurality of linear array transducer groups 132 in the X direction according to a certain delay control strategy such that the plurality of linear array transducer groups 132 may be successively excited in the X direction to transmit ultrasound beams in the ultrasound propagation direction F5 represented by the double-dotted line arrow, and the scanning plane in the scanning body formed by the propagation of the ultrasound beams in the three-dimensional space may be represented by the double-dotted line quadrilateral 15. The resultant ultrasound beams in the double-dotted line quadrilateral 15 may have steered angle φ within (0, 90 degree) and corresponding rotation angle θ of 180 degree. A delay control may be performed on the plurality of linear array transducer groups 131 in the Y direction according to a first delay control strategy such that the plurality of linear array transducer groups 132 may be simultaneously excited in the Y direction to transmit ultrasound beams in the ultrasound propagation direction F6 represented by the solid arrow, i.e., the time delay in the Y direction may be zero, and the scanning plane in the scanning body formed by the propagation of the ultrasound beams in the three-dimensional space may be represented by the solid line quadrilateral 16. The resultant ultrasound beams in this scanning body may have steered angle φ of 0 degree and corresponding rotation angle θ of 0 degree. A delay control may be performed on the plurality of linear array transducer groups 131 in the Y direction according to a second delay control strategy such that the plurality of linear array transducer groups 131 may be successively excited in the Y direction to transmit ultrasound beams in the ultrasound propagation direction F4 represented by the dashed line arrow, and the scanning plane in the scanning body formed by the propagation of the ultrasound beams in the three-dimensional space may be represented by the dashed line quadrilateral 14. The resultant ultrasound beams in this scanning body may have steered angle φ within (0, 90 degree) and corresponding rotation angle θ of 270 degree. FIG. 15 schematically shows three scanning bodies formed by scanning the scanning space in three ultrasound propagation directions. A certain delay control may be performed on the plurality of linear array transducer groups 131 in the Y direction such that the plurality of linear array transducer groups 131 may be successively excited in the Y direction to transmit ultrasound beams in the ultrasound propagation direction F8 represented by the solid arrow, and the scanning plane in the scanning body formed by the propagation of the ultrasound beams in the three-dimensional space may be represented by the solid line quadrilateral 18. The resultant ultrasound beams in the scanning body may have steered angle φ within (0, 90 degree) and corresponding rotation angle θ of 270 degree. A delay control may be performed on the plurality of linear array transducer groups 132 in the X direction according to a first delay control strategy such that the plurality of linear array transducer groups 132 may be successively excited in the X direction to transmit ultrasound beams in the ultrasound propagation direction F2 represented by the double-dotted line arrow, and the scanning plane in the scanning body formed by the propagation of the ultrasound beams in the three-dimensional space may be represented by the double-dotted line quadrilateral 12. The resultant ultrasound beams in this scanning body may have steered angle φ within (0, 90 degree) and corresponding rotation angle θ of 180 degree. A delay control may be performed on the plurality of linear array transducer groups 132 in the X direction according to a second delay control strategy such that the plurality of linear array transducer groups 132 may be successively excited in the X direction to transmit ultrasound beams in the ultrasound propagation direction F9 represented by the single-dotted line arrow, and the scanning plane in the scanning body formed by the propagation of the ultrasound beams in the three-dimensional space may be represented by the single-dotted line quadrilateral 19. The resultant ultrasound beams in this scanning body may have steered angle φ within (0, 90 degree) and corresponding rotation angle θ of 0 degree. Further, as shown in FIG. 17, based on FIG. 15, a delay control may be further performed on the plurality of linear array transducer groups 131 in the Y direction such that the plurality of linear array transducer groups 131 may be successively excited in the Y direction to transmit the ultrasound beams in the ultrasound propagation direction F10 represented by the dashed line arrow, and the scanning plane in the scanning body formed by the propagation of the ultrasound beams in the three-dimensional space may be represented by the dashed line quadrilateral 10. The resultant ultrasound beams in this scanning body may have steered angle φ within (0, 90 degree) and corresponding rotation angle θ of 90 degree.

In order to ensure the symmetry of the propagation directions mentioned above, in one embodiment, the delay control may be performed on each direction according to two delay control strategies which are used to implement the process in which the resultant ultrasound beams in two ultrasound propagation directions have the same steered angle φ and the difference between their corresponding rotation angle θ is 180 degree. By transmitting the ultrasound beams in the symmetrical manner described above, the three-dimensional flow field information of the volume in which the target point is located may be obtained using minimal spatial transmitting directions. In addition, with this kind of scanning, the scanning planes may have symmetry, such that the error of the echo signals obtained by transmitting the ultrasound beams in the ultrasound propagation directions may be consistent, which facilitate subsequent unified error compensation processing to the echo signals. Thereby the accuracy of the signal acquisition, and the accuracy of the tracking of the velocity vector of the target point, may be increased.

With the embodiment above, the probe 1 may use a small amount delay lines to perform the delay control. For example, each group of the linear array transducers may share one delay line. In one embodiment, the number of the delay lines used by the probe 1 may be the sum of the number of the groups of the linear array transducers in two directions. For example, as shown in FIG. 11A, there are 6 groups of linear array transducers 132 in the X direction, 6 groups of linear array transducers 131 in the Y direction, 9 groups of linear array transducers 133 in the Z direction, and 9 groups of linear array transducers 131 in the W direction. When the delay control is performed in the X direction and Y direction, at least 6+6=12 delay lines may be used.

Based on the embodiments above, a two-dimensional array probe with matrix arrangement may be used, and the X direction and Y direction may represent the longitudinal direction and the transverse direction of the two-dimensional array probe, respectively. Therefore, the process of respectively performing delay control on the plurality of groups of linear transducers of the part or all of the ultrasound wave transmitting transducers in two direction where in at least one direction performing the delay control according to at least two delay control strategies may include:

performing the delay control on the row linear array transducer groups of the part or all of the ultrasound wave transmitting transducers in the longitudinal direction according to at least one delay control strategy, and performing the delay control on the column linear array transducer groups of the part or all of the ultrasound wave transmitting transducers in the transverse direction according to at least two delay control strategy; or performing the delay control on the row linear array transducer groups of the part or all of the ultrasound wave transmitting transducers in the longitudinal direction according to at least two delay control strategy, and performing the delay control on the column linear array transducer groups of the part or all of the ultrasound wave transmitting transducers in the transverse direction according to at least one delay control strategy.

For example, in one embodiment, taking transmitting the plane ultrasound beam as an example, step 100 may include:

performing the delay control on the row linear array transducer groups of the part or all of the ultrasound wave transmitting transducers in the longitudinal direction according to at least one delay control strategy such that all of the column linear array transducer groups may transmit the plane ultrasound beams having at least one steered angle, which may be used to form at least one scanning body in the space in which the scanning target 12 is located; and performing the delay control on the column linear array transducer groups of the part or all of the ultrasound wave transmitting transducers in the transverse direction according to at least two delay control strategies such that all of the column linear array transducer groups may transmit the plane ultrasound beams having at least two steered angles, which may be used to form at least two scanning bodies in the space in which the scanning target 12 is located, where all of the scanning bodies may partially overlap; or performing the delay control on the row linear array transducer groups of the part or all of the ultrasound wave transmitting transducers in the longitudinal direction according to at least two delay control strategies such that all of the row linear array transducer groups may transmit the plane ultrasound beams having at least two steered angle, which may be used to form at least two scanning bodies in the space in which the scanning target 12 is located; and performing the delay control on the column linear array transducer groups of the part or all of the ultrasound wave transmitting transducers in the transverse direction according to at least one delay control strategy such that all of the column linear array transducer groups may transmit the plane ultrasound beams having at least one steered angle, which may be used to form at least one scanning body in the space in which the scanning target 12 is located; where all of the scanning bodies may partially overlap.

The steered angle herein may refer to the steered angle $\phi$ of the ultrasound propagation direction with respect to the normal of the transducer arrangement plane in the scanning plane mentioned above. Of course, the present disclosure will not be limited to the plane ultrasound beam. In the embodiments above, other ultrasound beams may also be used, such as the diffusion ultrasound beam or focused ultrasound beam, etc.

In addition, in the embodiments above, the shape of the transducer arrangement plane of the probe 1 will not be limited. For example, the ring two-dimensional array probe shown in FIG. 11C may be formed by a plurality of linear array transducer groups 115 arranged in radial direction, and the delay control may be performed on the plurality of linear array transducer groups respectively according to different delay control strategies in the clockwise or counterclockwise direction, etc. Of course, the linear array transducer group mentioned above will not be limited to the transducer array arranged linearly, but may also include the transducer array arranged in an arc or circle, such as the linear array transducer groups 116 arranged in the circumference direction or one circle of transducer array arranged in the circumference direction in the ring two-dimensional array prove shown in FIG. 11C. Similarly, in the embodiments above, performing the delay control on the plurality of linear array transducer groups of the part or all of the ultrasound wave transmitting transducers in different directions may be understood as performing the delay control on the plurality of linear array transducer groups 115 of the part or all of the ultrasound wave transmitting transducers in the circumference direction, or on the plurality of linear array transducer groups 116 of the part or all of the ultrasound wave transmitting transducers in the radial direction.

However, the order of the steps of the embodiments above will not be limited. During the process of implementing the transmitting of the ultrasound beams towards the scanning target in a plurality of ultrasound propagation directions by adjusting the steered angle $\phi$ and the rotation angle $\theta$ of the resultant ultrasound beams in the manner described above, the process of transmitting the ultrasound beams towards the scanning target in a certain ultrasound propagation direction to obtain a scanning body may be referred to as a first transmitting process, and the process of transmitting the ultrasound beams towards the scanning target in a certain ultrasound propagation direction once to obtain the corresponding scanning body once may be referred to as a first transmitting step. Therefore, step 100 above may include a plurality of first transmitting processes respectively in at least three ultrasound propagation direction. In order to facilitate the calculation of the velocity vector, in one embodiment, the first transmitting process in each ultrasound propagation direction may include performing the first transmitting steps at least twice, i.e., performing the first transmitting step of transmitting the ultrasound beams towards the scanning target at least twice in each ultrasound propagation direction. Therefore, each group of echo signals may include at least two echo signals, each of which may be derived from the echoes obtained by performing the first transmitting step once in one ultrasound propagation direction. For example, in the embodiments above, the process of performing the delay control on the plurality of linear array transducer groups of the part or all of the ultrasound wave transmitting transducers according to a certain delay control strategy in one direction to obtain a scanning body may be considered as the first transmitting process, and the process of performing once delay control on the plurality of linear array transducer groups of the part or all of the ultrasound wave transmitting transducers according to a certain delay control strategy in one direction to obtain once a corresponding scanning body may be considered as the first transmitting step. Since the first transmitting process in each ultrasound propagation direction may include performing the first transmitting step at least twice, the process of performing the delay control on the plurality of linear array transducer groups of the part or all of the ultrasound wave transmitting transducers according to a certain delay control strategy in one direction may include transmitting the ultrasound beams towards the scanning target at least twice.

In addition, in order to enable the echo data obtained to be used to calculate the blood velocity at the target point at the same moment, specifically, in one embodiment, the ultrasound beams may be alternately transmitted towards the scanning target based on the ultrasound propagation directions. For example, as shown in FIG. 19B, the first transmitting process of transmitting ultrasound beams towards the scanning target in a certain ultrasound propagation direction may include a plurality of first transmitting steps which may be alternately performed based on the ultrasound propagation directions as described above. A1 may represent performing once the first transmitting step in a first ultrasound propagation direction, A2 may represent performing once the first transmitting step in a second ultrasound propagation direction, and A3 may represent performing once the first transmitting step in a third ultrasound propagation direction. From left to right, the first transmitting steps may be alternately performed based on the ultrasound propagation directions. It may also be understood as performing the first transmitting step once successively in different ultrasound propagation directions, respectively, to form a repeating process, and repeating the repeating process. In connection with the embodiments in FIG. 15, A1 may represent performing the first transmitting step once in the ultrasound propagation direction F2 (represented by the double-dotted line arrow in FIG. 15), A2 may represent performing the first transmitting step once in the ultrasound propagation direction F8 (represented by the solid arrow in FIG. 15), and A3 may represent performing the first transmitting step once in the ultrasound propagation direction F9 (represented by the dotted line arrow in FIG. 15). From left to right, the process of respectively performing the first transmitting step once successively in the ultrasound propagation directions F2, F8 and F9 may be repeated.

Figure 19A:
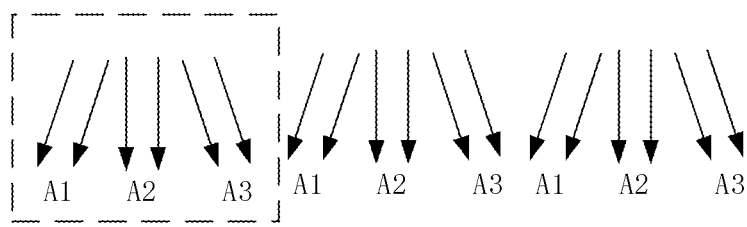
FIG. 19A and FIG. 19B schematically show methods for transmitting a plurality of ultrasound beams.
Figure 19B:
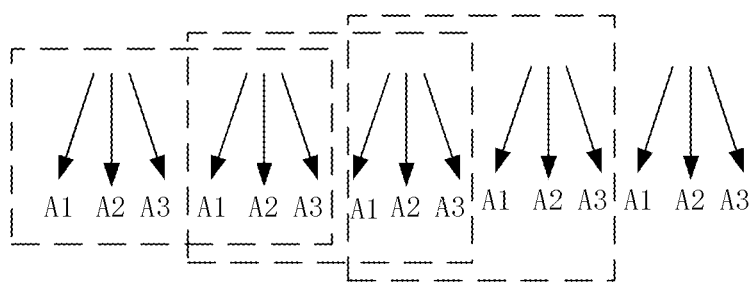

As another example, FIG. 19A shows the process of alternately transmitting ultrasound beams towards the scanning target based on the ultrasound propagation directions, where the first transmitting step is performed at least twice in each ultrasound propagation direction. In FIG. 19A, A1 may represent performing the first transmitting step twice in a first ultrasound propagation direction, A2 may represent performing the first transmitting step twice in a second ultrasound propagation direction, and A3 may represent performing the first transmitting step twice in a third ultrasound propagation direction. A1, A2 and A3 may be alternately performed based on the ultrasound propagation directions. In connection with the embodiments shown in FIG. 14, A1 may represent successively performing the first transmitting step twice in the ultrasound propagation direction F5 (represented by the double-dotted line arrow in FIG. 14), A2 may represent successively performing the first transmitting step twice in the ultrasound propagation direction F4 (represented by the dashed line arrow in FIG. 14), and A3 may represent successively performing the first transmitting step twice in the ultrasound propagation direction F6 (represented by the solid arrow in FIG. 14). From left to right, the process of respectively successively performing the first transmitting step twice in the ultrasound propagation directions F5, F4 and F6 may be repeated. FIG. 19A may also be considered as repeating processes, and step 100 may include a process of repeatedly performing the repeating process for a plurality of times. Each repeating process may include the process of successively performing the first transmitting step twice in three ultrasound propagation directions, respectively.

Figure 20:
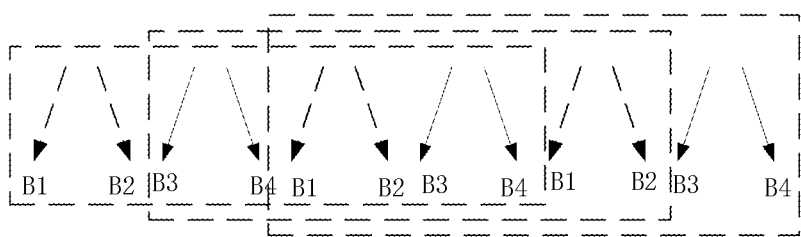
FIG. 20 schematically shows a technique for transmitting the ultrasound beams in four ultrasound propagation directions.

Alternatively, the adjacent two transmitting of the ultrasound beams may be in two different ultrasound propagation directions, as shown in FIG. 20 and FIG. 19B. In FIG. 20, B1, B2, B3 and B4 may represent the processes of performing the first transmitting step once in four ultrasound propagation directions, respectively. From left to right, the first transmitting steps may be alternately performed based on the ultrasound propagation directions. In connection with the embodiments shown in FIG. 17, B1 may represent performing the first transmitting step once in the ultrasound propagation direction F2 (represented by the double-dotted line arrow in FIG. 17), B2 may represent performing the first transmitting step once in the ultrasound propagation direction F8 (represented by the solid arrow in FIG. 17), B3 may represent performing the first transmitting step once in the ultrasound propagation direction F9 (represented by the dotted line arrow in FIG. 17), and B4 may represent performing the first transmitting step once in the ultrasound propagation direction F10 (represented by the dashed line arrow in FIG. 17). One first transmitting step may be performed respectively in the ultrasound propagation directions F2, F8, F9 and F10 to form a repeating process, and then the repeating process may be performed repeatedly.

Based on the alternate transmitting scheme of the embodiments above, in one embodiment, a two-dimensional array probe with matrix arrangement may be used, and the process of performing delay control on the plurality of linear array transducer groups of the part or all of the ultrasound wave transmitting transducers respectively in two directions where in at least one direction the delay control may be performed respectively according to at least two delay control strategies may include repeatedly performing the following steps for a plurality of times:

first, performing the delay control on the row linear array transducer groups of the part or all of the ultrasound wave transmitting transducers in the longitudinal direction according to a first delay control strategy such that all of the column linear array transducer groups may transmit resultant ultrasound beams having a first steered angle which may be used to form a first scanning body at least once in the space in which the scanning target 12 is located;

thereafter, performing the delay control on the column linear array transducer groups of the part or all of the ultrasound wave transmitting transducers in the transverse direction according to a third delay control strategy such that all of the row linear array transducer groups may transmit resultant ultrasound beams having a second steered angle which may be used to form a second scanning body at least once in the space in which the scanning target 12 is located; and finally, performing the delay control on the row linear array transducer groups of the part or all of the ultrasound wave transmitting transducers in the longitudinal direction according to a second delay control strategy such that all of the column linear array transducer groups may transmit resultant ultrasound beams having a third steered angle which may be used to form a third scanning body at least once in the space in which the scanning target 12 is located.

In the embodiment above, the transmitting in three ultrasound propagation directions may be implemented. Further, in order to implement symmetrical transmitting, the first delay control strategy and the second delay control strategy may be used to obtain resultant ultrasound beams which have the same steered angle $\phi$ and of which the difference between the rotation angles $\theta$ is 180 degree.

Similarly, in another embodiment, the process performed repeatedly above may further include: performing the delay control on the column linear array transducer groups of the part or all of the ultrasound wave transmitting transducers in the transverse direction according to a fourth delay control strategy such that all of the row linear array transducer groups may transmit resultant ultrasound beams having a fourth steered angle which may be used to form a fourth scanning body at least once in the space in which the scanning target 12 is located. In the present embodiment, the transmitting in four ultrasound propagation directions may be implemented. Further, in order to implement symmetrical transmitting, the third delay control strategy and the fourth delay control strategy may be used to obtain resultant ultrasound beams which have the same steered angle $\phi$ and of which the difference between the corresponding rotation angles $\theta$ is 180 degree. For example, as shown in FIG. 17, the first scanning body may be formed by scanning planes 18, the second scanning body may be formed by scanning planes 12, the third scanning body may be formed by scanning planes 10, and the fourth scanning body may be formed by scanning planes 19.

In step 200, the receiving circuit 4 and the beamforming unit 5 may receive the echoes of the ultrasound beams transmitted in step 100 above to obtain at least three groups of echo signal. Each group of echo signal may be derived from the ultrasound beams transmitted in one ultrasound propagation direction. Specifically, the first transmitting step of transmitting the ultrasound beams towards the scanning target may be performed at least twice in each ultrasound propagation direction. Each time the first transmitting step is performed, the echo signals may be obtained once. Correspondingly, each group of echo signals may include at least two echo signals, each of which may be derived from the echoes obtained by performing the first transmitting step once in one ultrasound propagation direction. At least one of the echo signals may be processed to obtain one frame of ultrasound image, which may be one frame of three-dimensional image or a three-dimensional image formed by a plurality of two-dimensional images. For example, during the first transmitting process in which the ultrasound beams are transmitted towards the scanning target in one ultrasound propagation direction such that the ultrasound beams propagate in the space in which the scanning target is located to form a scanning body, the echoes of the ultrasound beams generated by the scanning body may be received to obtain one group of echo signal. And, during the first transmitting step in which the ultrasound beams are transmitted towards the scanning body in one ultrasound propagation direction once such that the ultrasound beams propagate in the space in which the scanning target is located to form the corresponding scanning body once, the echoes of the ultrasound beams generated by the scanning body may be received to obtain the echo signal once. In order to enable the subsequent effective calculation of the velocity component of the target point, each group of echo signal may include at least two echo signal.

Because the plane ultrasound beam may enable high frame rate and thus the velocity components may be calculated in real time, plane ultrasound beams may be used to obtain the echo signals used to calculate the velocity components in following steps. Therefore, in one embodiment, in step 100, plane ultrasound beams may be transmitted towards the scanning target in at least three ultrasound propagation directions; and in step 200, the echoes of the plane ultrasound beams may be received to obtain at least three groups of plane beam echo signal and each group of plane beam echo signal may be derived from the plane ultrasound beams transmitted in one ultrasound propagation direction.

Furthermore, as shown in FIG. 8, the ultrasound beams may be transmitted in the direction indicated by the dot-chain arrow 261, and corresponding echoes may be received in the direction indicated by the dot-chain arrow 262 to obtain the echo signal, or, the corresponding echoes may also be received in the direction indicated by the dot-chain arrow 261 shown in FIG. 8 to obtain the echo signal, which is well known in the art and will not be described in detail. However, in step 200, it should be understood that the echoes derived from the ultrasound beams transmitted in step 100 may be received in any direction to obtain the corresponding echo signals.

In step 300, a data processing unit 9 may calculate one velocity component of the target point in the scanning target using one of the at least three groups of echo signals. Since the plane ultrasound beams may enable high frame rate and the velocity component may be calculated in real time, the echo signals of the plane ultrasound beams may be used to calculate the velocity component. Therefore, in one embodiment, in step 300, one velocity component of the target point may be calculated using one of the groups of plane beam echo signals, and thus at least three velocity components may be obtained using the at least three groups of plane beam echo signals. Each group of echo signals may be used to calculate a velocity component in one ultrasound propagation direction. In the embodiments, a plurality of methods may be used to calculate one velocity component of the target point using the obtained echo signals.

The first transmitting step in which the plane ultrasound beams are transmitted towards the scanning target may be performed at least twice in each ultrasound propagation direction. Each group of plane beam echo signals may include at least two plane beam echo signals each of which may be derived from the echoes obtained by performing the first transmitting step once in one ultrasound propagation direction. Based on the at least two plane beam echo signals in each group of plane beam echo signal, the velocity component in one ultrasound propagation direction may be calculated using the following methods.

First, the at least two echo signals in one of the groups of echo signal may be acquired to obtain two frames of ultrasound image data (herein, one frame of ultrasound image data may be understood as one frame of three-dimensional image data or a three-dimensional image data formed by a plurality of two-dimensional image data). The one of the groups of echo signal may be derived from the ultrasound beams transmitted in one ultrasound propagation direction. The two frames of ultrasound image data herein may be two adjacent frames of ultrasound image data.

Thereafter, the velocity component of the target point in one ultrasound propagation direction at a first moment may be calculated based on the two frames of ultrasound image data. For example, generally, in ultrasound imaging, a Doppler processing using Doppler principle may be performed on the ultrasound echo signals to obtain the velocity of the scanning target or the moving parts therein. For example, after the ultrasound echo signals are obtained, the velocity of the scanning target or the moving parts therein may be obtained based on the ultrasound echo signals using an autocorrelation estimation method or a cross-correlation estimation method. In one embodiment, the methods of performing Doppler processing on the ultrasound echo signals to obtain the velocity of the scanning target or the moving parts therein may be used to calculate a velocity component using one of the groups of echo signal. The details thereof may be as the following.

In Doppler ultrasound imaging, the ultrasound beams may be successively transmitted towards the scanning target in a same spatial direction for a plurality of times, and the echoes of the ultrasound beams in this spatial direction may be received for a plurality of times to obtain a plurality of echo signals. Each value in each echo signal may correspond to a value of a target point when the scanning is performed in one ultrasound propagation direction. Thereafter, a Hilbert transform may be performed on the plurality of echo signals respectively in the ultrasound propagation directions to obtain a plurality of groups of image data in which the value of each target point may be represented by complex number. After transmitting and receiving for N times, there may be N complex values varying in time at each target point. Next, a velocity of a target point z in an ultrasound propagation direction may be calculated using following two formulas:

$$v_z = -\frac{c}{4\pi f_0 T_{prf}} \arctan\left(\frac{\Im\{R(1)\}}{\Re\{R(1)\}}\right) \quad \text{formula (1)}$$

$$R(1) = \frac{1}{N-1} \sum_{i=0}^{N-2} x(i)x(i+1) + y(i)y(i+1) + j[y(i+1)x(i) - x(i+1)y(i)] \quad \text{formula (2)}$$

Where Vz is the velocity value calculated in the ultrasound propagation direction, c is sound velocity, f0 is center frequency of the probe, Tprf is time interval between two transmitted ultrasound beams, N is number of times of the transmitting, j is imaginary unit, x(i) is real part of the i-th transmitting, y(i) is imaginary part of the i-th transmitting, $\Im$ is taking-imaginary part operator, and $\Re$ is taking-real part operator. The formulas above may be used to calculate the velocity at a fixed position.

And then, similarly, the velocity of each target point may be calculated using the N complex values.

Finally, the direction of the velocity of the blood may be the ultrasound propagation direction.

In addition, methods such as spot tracking method may also be used to obtain the velocity component of the target point in one ultrasound propagation direction at a certain moment based on two frames of ultrasound image data. Of course, any methods which are or will be used in the art and can calculate the velocity of the scanning target or the moving parts therein using ultrasound echo signals may also be used and will not be described in detail herein.

In step 400, the data processing unit 9 may obtain the velocity vector of the target point using at least three velocity components calculated in step 300, where the at least three ultrasound propagation directions corresponding to the at least three groups of echo signal used for calculating the at least three velocity components may not be in a same plane, referring to the description above with respect to step 100. In one embodiment, step 400 may include following steps.

First, the velocity components of the target point in at least three ultrasound propagation directions at a first moment may be acquired.

Thereafter, the velocity vector of the target point at the first moment may be obtained by velocity synthesis using the velocity components in the at least three ultrasound propagation directions at the first moment.

As another example, in the case that, in step 100, the ultrasound beams are transmitted towards the scanning target in N (N is greater than or equal to 3) ultrasound propagation directions, N groups of echo signal may be obtained and there may be N velocity components at each moment.

When the ultrasound beams in the N ultrasound propagation directions are alternately transmitted according to the ultrasound propagation direction, the N velocity components respectively corresponding to different moments may also be calculated repeatedly at the same time, and each time the N velocity components are obtained, the synthesis of the velocity components may be performed to obtain the velocity vector of the target point at current moment for one time. In one embodiment, the calculated velocity vector of the target point may be closer to the actual flow velocity in the flow field in the three-dimensional space by using more than three ultrasound propagation directions or increasing the number of the used ultrasound propagation directions. Therefore, each time the velocity vector of the target point is calculated in real time, the echo signals corresponding to all of the ultrasound propagation directions may be taken into account such that the velocity vector of the target point calculated in real time may be closer to the actual value. Hereinafter, the process of the present embodiment in which the echo signals corresponding to all of the ultrasound propagation directions are used to calculate the velocity vector of the target point for one time may be referred to as longest calculation period of target point velocity vector, i.e., the process of respectively calculating, using the process of calculating one velocity component of the target point in the scanning target based on one of at least three groups of echo signals in step 300 described above, the velocity components of the target point in all of the ultrasound propagation directions corresponding to the at least three groups of echo signal and synthesizing the velocity components in all of the ultrasound propagation directions to obtain the velocity vector of the target point. In this case, as long as all of the ultrasound propagation directions used in the process of transmitting ultrasound beams towards the scanning target in at least three ultrasound propagation directions in step 100 are not in a same plane, the constraint of the normal lines being not in a same plane in step 300 above may be satisfied.

In addition, the calculation of the velocity vector of the target point described above may also be simplified. In a specific embodiment, when N is greater than or equal to 3, in order to increase the calculation speed of the velocity vector, the velocity vector of the target point at current moment may be obtained by velocity synthesis using the velocity components at the current moment in at least three ultrasound propagation directions in step 400 above. Specifically, during the calculation of the velocity vector, the velocity vector may be calculated for one time only using three velocity components successively obtained, where the three ultrasound propagation directions corresponding to the three groups of echo signals used for calculating said three velocity components are not in a same plane. Therefore, in one embodiment, the three groups of echo signals which are successively received in chronological order may be derived from the ultrasound beams transmitted in three different ultrasound propagation directions, and, in step 400 above, the velocity vector of the target point may be obtained by velocity synthesis using the velocity components of the target point at a same moment in the three ultrasound propagation directions. In the present embodiment, the time for calculating the three-dimensional velocity vector of the target point each time may be reduced, the efficiency of the real time calculation of the velocity vector may be increased, and the continuity of display of the velocity vector of the target point may be ensured. Hereinafter, the process of calculating the velocity vector of the target point for one time using there velocity components in the present embodiment may be referred to as shortest calculation period of target point velocity vector, i.e., the process of respectively calculating the velocity components in the three ultrasound propagation directions corresponding to the three groups of echo signals received successively and synthesizing the velocity vector of the target point using the velocity components in the three ultrasound propagation directions.

For the case between the shortest and the longest calculation periods of target point velocity vector described above, in step 400, the velocity components of the target point in at least three ultrasound propagation directions corresponding to at least three groups of echo signals received successively may be respectively calculated using the process of calculating one velocity component of the target point in the scanning target based on one of the at least three groups of echo signals, and the velocity vector of the target point may be obtained by synthesis using the velocity components at the at least three ultrasound propagation directions. In this case, as long as, in the process of transmitting the ultrasound beams towards the scanning target in at least three ultrasound propagation directions in step 100 above, the adjacent at least three ultrasound propagation directions are not in a same plane, the constraint of the normal lines being not in a same plane in step 300 above may be satisfied.

The velocity vector synthesis in the shortest calculation period of target point velocity vector will be described in detail with reference to FIG. 14 hereinafter. In the embodiment shown in FIG. 14, the velocity component V4 is a velocity in the ultrasound propagation direction F4, and the velocity component V6 is a velocity in the ultrasound propagation direction F6. The two velocity components may be synthesized to obtain a velocity component V1. The velocity component V5 in the ultrasound propagation direction F5 may be synthesized with the velocity component V1 to obtain the desired velocity vector V0. The synthesis methods of two velocity components herein may also be used in the longest calculation period of target point velocity vector described above and any velocity vector synthesis between the shortest and the longest calculation periods.

In the present disclosure, the design of the calculation period of target point velocity vector is not limited to the two techniques described above. For example, the velocity components in more than 3 and less than 10 ultrasound propagation directions at any moment may be used to synthesize the velocity vector of the target point at this moment. By adjusting the number of the ultrasound propagation directions used in a single calculation period of target point velocity vector, the accuracy of the calculation of the three-dimensional velocity vector of the target point may be adjusted. As shown in FIG. 19A, 19B and FIG. 20, in the execution order from left to right, the echo signals obtained by the plurality of first transmitting steps in the dashed box may be used to calculate the velocity vector for one time. Therefore, in one embodiment, after the first transmitting step is successively performed twice in each of the ultrasound propagation directions, step 300 and step 400 may be performed once to obtain the velocity vector for one time. The more the velocity components used in a single calculation of the velocity vector, the higher the accuracy of the calculation, but the imaging speed may thus be limited. Therefore, in one embodiment, a dialog box, a button, a prompt or the like may be provided for the user, and the number of the ultrasound propagation directions selected by the user may be obtained, with which an instruction may be generated. Based on the instruction, the number of the ultrasound propagation directions to be used in the ultrasound imaging may be adjusted, and the number of the velocity components to be used for synthesizing the velocity vector of the target point may be determined according to the number of the ultrasound propagation directions. Alternatively, a dialog box, a button, a prompt or the like may be provided for the user, and the number of the velocity components to be used for synthesizing the velocity vector of the target point selected by the user may be obtained, with which an instruction may be generated. Based on the instruction, the number of the velocity components to be used for synthesizing the velocity vector of the target point may be adjusted, or the number of the ultrasound propagation directions in step 100 above may be adjusted according to the number of the velocity components, thereby achieving a custom setting of the display effect of the ultrasound imaging.

In step 500, the data processing unit 9 may obtain the ultrasound image of at least a portion of the scanning target using the at least three groups of echo signals, or using focused ultrasound beam echo signals obtained by transmitting focused ultrasound beams towards the scanning target. The ultrasound image herein may be B mode image, color image or the like. In step 500, the ultrasound image may be obtained using the plurality of echo signals in one of the groups of echo signals. In the case that plane ultrasound beams are transmitted in step 100, the ultrasound image may be obtained using at least three groups of plane beam echo signals. Because quality of the image obtained using plane ultrasound beams is lower than quality of the image obtained using focused ultrasound beams, the method may further include following steps in order to obtain a higher quality image:

transmitting focused ultrasound beams towards the scanning target; and receiving the echoes of the focused ultrasound beams to obtain focused ultrasound beam echo signals.

Hence, in step 500, the ultrasound image of at least a portion of the scanning target may be obtained using the focused ultrasound beam echo signals.

The method for obtaining the ultrasound image using corresponding echo signals may be any suitable method which is or will be used in the art, and will not be described in detail herein.

In the embodiments above, any transmitted ultrasound beam whose type is not specifically limited may be any one of a plane ultrasound beam, a diffusion ultrasound beam, and a focused ultrasound beam, etc. When the type of the ultrasound beam is changed, the echo signals will be also changed correspondingly. For example, in the case that the focused ultrasound beams are transmitted in step 100, the echo signals in subsequent steps will be "focused ultrasound beam echo signals," and so on.

In addition, in order to synchronize the calculation of the velocity vector and the obtaining of the ultrasound images, when obtaining the ultrasound images using the focused ultrasound beams, at least one of the step of transmitting the focused ultrasound beams towards the scanning target may be inserted between the processes of transmitting ultrasound beams towards the scanning target in at least three ultrasound propagation directions. The focused ultrasound beams may be used to obtain ultrasound images with high quality, while other ultrasound beams may be used to obtain the real velocity vector of the target point. The insertion of the focused ultrasound beams may be similar to those in the embodiments with respect to "inserting focused ultrasound beam transmitting processes between plane ultrasound beam transmitting processes" below, where the plane ultrasound beams in the embodiments of the insertion describe below are replaced by the ultrasound beams transmitted in step 100 above, which will not be described in detail herein.

In step 600, the ultrasound images obtained in step 500 and the velocity vectors obtained in step 400 may be displayed. After the velocity vectors of the target points and the ultrasound images of at least a portion of the scanning target are obtained, the velocity vectors and the ultrasound images may be simultaneously displayed on the display 8. For example, in one embodiment, the velocity vectors may be superimposed on the ultrasound images. In addition, because the actual speed of the velocity vector is greater than the speed available for human eye, when displaying the velocity vectors, the speed magnitude of the velocity vectors may be reduced by a certain times.

Figure 21:
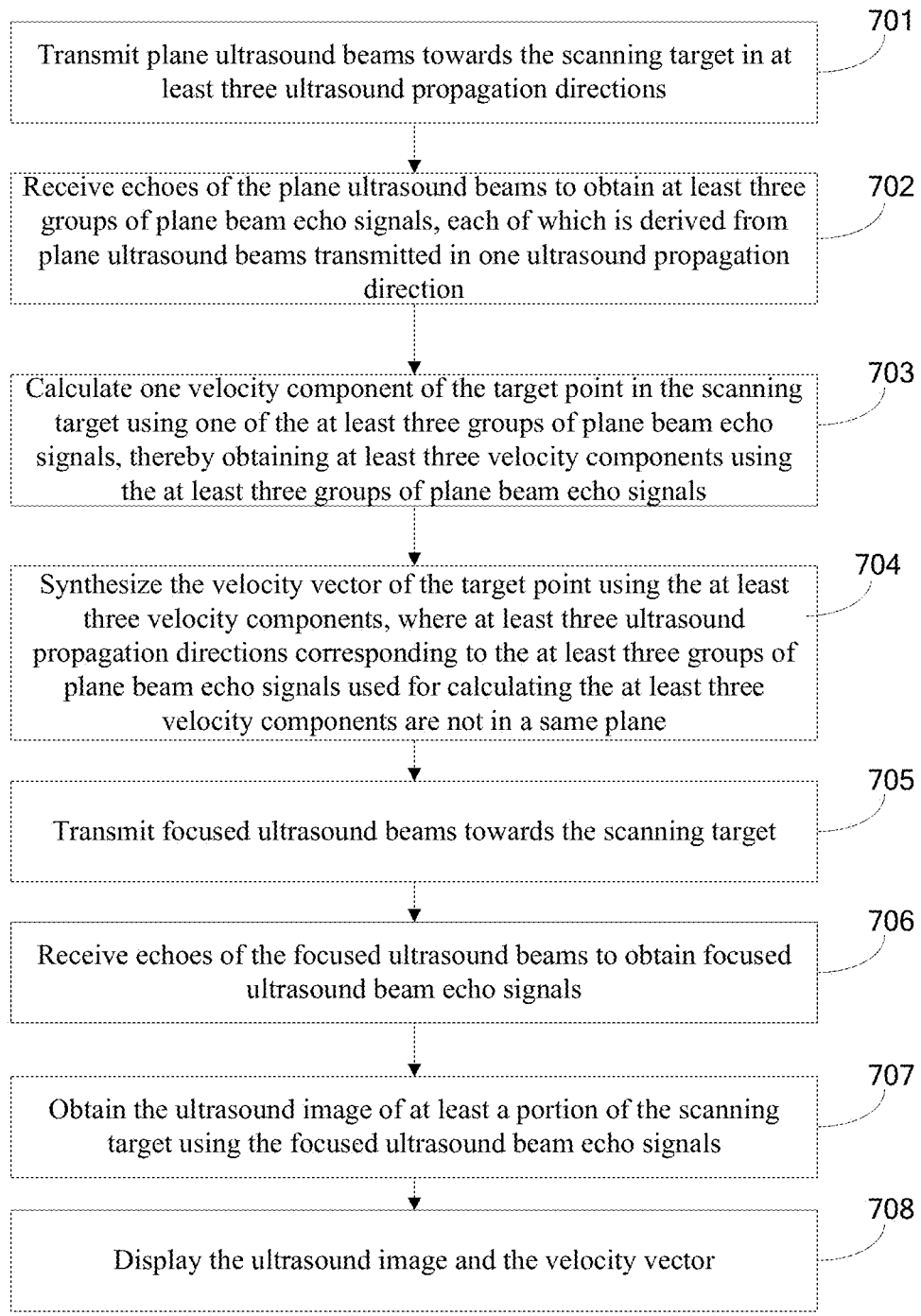
FIG. 21 is a flow chart of an ultrasound imaging method.

In step 100 above, one type of ultrasound beam may be used, such as the plane ultrasound beam, and hence the "echo signals" in other steps may be the echo signals corresponding thereto. For example, when the plane ultrasound beams are transmitted, the echo signals may be plane beam echo signals; when the focused ultrasound beams are transmitted, the echo signals may be the focused beam echo signals; and so on. In order to increase the quality of the image of the ultrasound imaging and increase the calculation speed of the velocity vectors, in one embodiment, the plane ultrasound beams may be transmitted to obtain the ultrasound echo signals used for calculating the velocity vectors, while the focused ultrasound beams may be transmitted to obtain the ultrasound images. Specifically, as shown in FIG. 21, the ultrasound imaging method may include following steps.

In step 701, the transmitting circuit 2 may excite the probe 1 to transmit plane ultrasound beams towards the scanning target in at least three ultrasound propagation directions.

In step 702, the receiving circuit 4 and the beamforming unit 5 may receive the echoes of the plane ultrasound beams to obtain at least three groups of plane beam echo signals. Each group of plane beam echo signals may be derived from the plane ultrasound beams transmitted in one ultrasound propagation direction.

In step 703, the data processing unit 9 may calculate one velocity component of the target point in the scanning target using one of the at least three groups of plane beam echo signal, and thereby obtain at least three velocity components using the at least three groups of plane beam echo signal.

In step 704, the data processing unit 9 may synthesize the velocity vector of the target point using the at least three velocity components, where the at least three ultrasound propagation directions corresponding to the at least three groups of echo signal used for calculating the at least three velocity components are not in a same plane.

In step 705, the transmitting circuit 2 may excite the probe 1 to transmit focused ultrasound beams towards the scanning target.

In step 706, the receiving circuit 4 and the beamforming unit 5 may receive the echoes of the focused ultrasound beams to obtain focused ultrasound beam echo signals.

In step 707, the data processing unit 9 may obtain ultrasound images of at least a portion of the scanning target using the focused ultrasound beam echo signals.

In step 708, the ultrasound images and the velocity vectors may be displayed on the display 8.

In the present embodiment, only the type of the ultrasound beam is specifically described in steps 701 to 704 with reference to steps 100 to 400 above. The specific embodiments and various combination embodiments may be similar to those with respect to steps 100 to 400 described above. For example, the specific embodiments and various combination embodiments of steps 701 to 704 may be obtained based on those described previously by replacing the ultrasound beams and echo signals in steps 100 to 400 described above with "plane ultrasound beams" and "plane beam echo signals" and the like, which will not be described in detail herein.

In addition, in step 707, the ultrasound images may be three-dimensional ultrasound images or two-dimensional ultrasound images. In order to obtain ultrasound images with higher quality, the focused ultrasound beams may be transmitted for a plurality of times to obtain one frame of ultrasound image. Therefore, in one embodiment, step 705 may include a plurality of second transmitting steps of transmitting focused ultrasound beams towards the scanning target. The second transmitting step may represent a process of transmitting focused ultrasound beam towards the scanning target for one time. The combination of the plane ultrasound beam transmitting and the focused ultrasound beam transmitting will be described in detail below.

In order to ensure the consistency in time of the obtained ultrasound image of at least a portion of the scanning target and the obtained velocity vector of the target point, in one embodiment, at least one second transmitting step of transmitting focused ultrasound beam towards the scanning target may be inserted between the processes of transmitting a plane ultrasound beams towards the scanning target in at least three ultrasound propagation directions. In the present embodiment, ultrasound image with high quality may be obtained by transmitting the focused ultrasound beams for a plurality of times, and the resolution of the ultrasound image may be increased. The processes of transmitting a plane ultrasound beams towards the scanning target in at least three ultrasound propagation directions may be similar to those in step 100 described above and will not be described in detail herein.

In order to ensure that minimum signal data for calculating the velocity vector can be obtained, a third transmitting step of transmitting a plane ultrasound beam towards the scanning target may be performed twice in each ultrasound propagation direction, and each group of plane beam echo signals may include two plane beam echo signals each of which is derived from the echoes obtained by performing the third transmitting step for one time in one ultrasound propagation direction. Therefore, transmitting the plane ultrasound beam towards the scanning target once in one ultrasound propagation direction may be referred to as a third transmitting step, and transmitting the plane ultrasound beams towards the scanning target in one ultrasound propagation direction may be referred to as a third transmitting process, and the same below. The embodiments of the insertion of the focused ultrasound beam transmitting between the plane ultrasound beam transmitting will be described in detail below.

For example, as shown in FIG. 25, during transmitting a plane ultrasound beams towards the scanning target alternately according to different ultrasound propagation directions as shown in FIG. 19A, the second transmitting step of transmitting focused ultrasound beam towards the scanning target may be inserted for at least one time. Specifically, the third transmitting step of transmitting a plane ultrasound beam towards the scanning target may be successively performed at least twice in a same ultrasound propagation direction, and the second transmitting step may be inserted between the adjacent two third transmitting steps for at least one time. As shown in FIG. 25, a thin solid arrow with different direction may represent one third transmitting step performed in different ultrasound propagation direction, and a thick solid arrow may represent one second transmitting step performed. As shown in FIG. 25B, at least one second transmitting step may be inserted between the adjacent two third transmitting steps. In another embodiment, as shown in FIG. 25A, the two third transmitting steps adjacent to the inserted at least one second transmitting step may belong to a third transmitting process of transmitting a plane ultrasound beams towards the scanning target in different ultrasound propagation directions. As shown in FIG. 15C, the two third transmitting steps adjacent to the inserted at least one second transmitting step may belong to a third transmitting process of transmitting a plane ultrasound beams towards the scanning target in a same ultrasound propagation direction. In addition, in one embodiment, a third transmitting process of transmitting a plane ultrasound beams towards the scanning target in at least two ultrasound propagation directions may exist between two adjacent inserted second transmitting steps. Specifically, as shown in FIG. 25D, the process of performing the third transmitting step at least twice respectively in three ultrasound propagation directions may exist between two adjacent inserted second transmitting steps.

As another example, in the case that the process of transmitting a plane ultrasound beams towards the scanning target in each ultrasound propagation direction includes a plurality of third transmitting steps which are alternately performed according to the different ultrasound propagation directions, as shown in FIG. 19B and FIG. 20, the focused ultrasound beam transmitting may be inserted at least as using the techniques shown in FIG. 22. In FIG. 22, the execution order may be from left to right. One thin solid arrow or dotted arrow may represent one performed third transmitting step used for transmitting a plane ultrasound beam. The thin solid arrows or dotted arrows with different pointing directions, and the arrows with dotted line and arrows with solid line, may represent the third transmitting steps performed in different ultrasound propagation directions. One thick solid arrow may represent one performed second transmitting step used for transmitting focused ultrasound beam. As shown in FIG. 22E, one second transmitting step may be inserted between two adjacent third transmitting steps. In FIG. 22A, three second transmitting steps may be inserted between two adjacent third transmitting steps, and seven third transmitting steps may exist between two adjacent inserted second transmitting steps. In FIG. 22B, one second transmitting step may be inserted between two adjacent third transmitting steps, and three third transmitting steps may exist between two adjacent inserted second transmitting steps. In FIG. 22D, one second transmitting step may be inserted between two adjacent third transmitting steps, and two third transmitting steps may exist between two adjacent inserted second transmitting steps. In FIG. 22C, two second transmitting steps may be inserted between two adjacent third transmitting steps, and six third transmitting steps may exist between two adjacent inserted second transmitting steps. Therefore, in one embodiment, when alternately performing the third transmitting steps according to different ultrasound propagation directions, at least one second transmitting step may be inserted between two adjacent third transmitting steps. Specifically, the third transmitting process of transmitting a plane ultrasound beams towards the scanning target in at least two ultrasound propagation directions may exist between two adjacent inserted second transmitting steps. Further, at least two third transmitting steps in different ultrasound propagation directions may exist between two adjacent inserted second transmitting steps. Accordingly, the focused ultrasound beam transmitting may not affect the normal transmitting sequence of the plane ultrasound beams and avoid the interference to the receiving and subsequent processing of the plane ultrasound echo signals. If too many second transmitting steps of transmitting the focused ultrasound beam were inserted for a single time, the time for obtaining the velocity vector of the target point in a three-dimensional space using the plane ultrasound beams may be delayed, and the calculation accuracy of the velocity vector may be affected. Therefore, in another embodiment, one to three second transmitting steps may be inserted between two adjacent third transmitting steps.

Figure 22A:
FIG. 22A, FIG. 22B, FIG. 22C, FIG. 22D, and FIG. 22E schematically show techniques for inserting the focused ultrasound beam transmitting between a plurality of plane ultrasound beam transmitting.
Figure 22B:
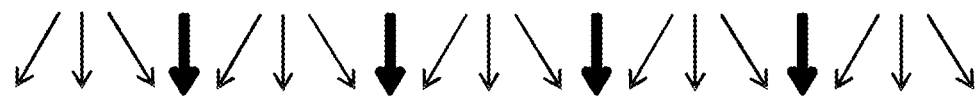
Figure 22C:
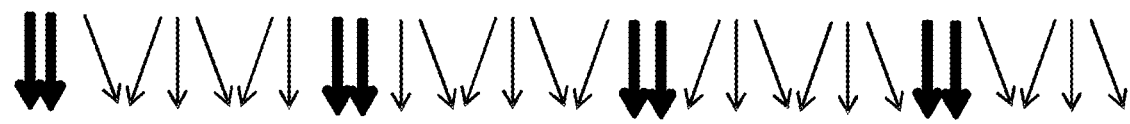

Based on this, as shown in FIG. 22C, in one embodiment, one third transmitting step may be added before or after the inserted second transmitting step, such that the two third transmitting steps adjacent to the inserted at least one second transmitting step may both belong to a process of transmitting a plane ultrasound beams towards the scanning target in a same ultrasound propagation direction. This embodiment may be particularly suitable for the case that more than one second transmitting steps inserted in a single insertion, and may enable the interval between two inserted second transmitting steps to be one shortest calculation period of target point velocity sector, thereby increasing the imaging speed of the images. In addition, this embodiment may also be particularly suitable for the case that the process of transmitting a plane ultrasound beams towards the scanning target in at least three ultrasound propagation directions exists between two adjacent inserted second transmitting steps, particularly the case that the third transmitting steps in at least three ultrasound propagation directions corresponding to the at least three velocity components used for calculating the velocity vector for one time exists between two adjacent inserted second transmitting steps, and specifically the case that the process of performing the third transmitting step at least twice respectively in three ultrasound propagation directions exists between two adjacent inserted second transmitting steps. Accordingly, the three-dimension space velocity vector of the target point at corresponding position may be displayed just after one frame of image is obtained using the focused ultrasound beams in order to reduce the time difference of information tracking between the ultrasound images and the velocity vectors of the target point, such that the ultrasound images and the velocity vectors of the target points may be displayed synchronously as much as possible, and the display accuracy of the ultrasound images and the velocity vectors of the target points may be increased.

For example, with reference to the embodiments shown in FIG. 14, FIG. 15 and FIG. 16 and the transmitting sequence in FIG. 22B, in one embodiment, the plane ultrasound beams and the focused ultrasound beams may be transmitted in three ultrasound propagation directions according to the following repetitive processes. Each repetitive process may include following steps.

First, the ultrasound beams may be transmitted towards the scanning target once in a first ultrasound propagation direction to form a first scanning body once. The first ultrasound propagation direction may be the direction F5 or F2 shown in FIG. 14, FIG. 15 or FIG. 16.

Thereafter, the plane ultrasound beams may be transmitted towards the scanning target once in a second ultrasound propagation direction to form a second scanning body once. The second ultrasound propagation direction may be the direction F4, F8 or F6 shown in FIG. 14, FIG. 15 or FIG. 16.

Next, the plane ultrasound beams may be transmitted towards the scanning target once in a third ultrasound propagation direction to form a third scanning body once. The third ultrasound propagation direction may be the direction F6, F9 or F21 shown in FIG. 14, FIG. 15 or FIG. 16.

The focused ultrasound beams may be then transmitted towards the scanning target at least once.

Figure 22D:
Figure 22E:
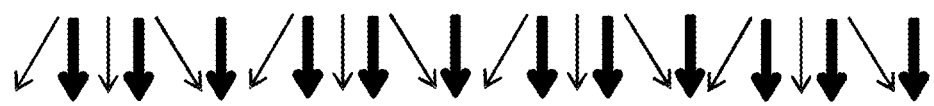

As another example, with reference to the embodiments shown in FIG. 17 and FIG. 18 and the transmitting sequence in FIG. 22D, in one embodiment, the plane ultrasound beams and the focused ultrasound beams may be transmitted in four ultrasound propagation directions according to the following repetitive processes. Each repetitive process may include following steps.

First, the plane ultrasound beams may be transmitted towards the scanning target once in a first ultrasound propagation direction to form a first scanning body once. The first ultrasound propagation direction may be the direction F2 shown in FIG. 17 and FIG. 18.

Thereafter, the plane ultrasound beams may be transmitted towards the scanning target once in a second ultrasound propagation direction to form a second scanning body once. The second ultrasound propagation direction may be the direction F9 shown in FIG. 17 and FIG. 18.

Next, the focused ultrasound beams may be transmitted towards the scanning target at least once.

Thereafter, the plane ultrasound beams may be transmitted towards the scanning target once in a third ultrasound propagation direction to form a third scanning body once. The third ultrasound propagation direction may be the direction F8 shown in FIG. 17 and FIG. 18.

The plane ultrasound beams may be then transmitted towards the scanning target once in a fourth ultrasound propagation direction to form a fourth scanning body once. The fourth ultrasound propagation direction may be the direction F10 or F21 shown in FIG. 17 and FIG. 18.

Similarly, with reference to the embodiments shown in FIGS. 14 to 18 and the transmitting sequence in FIG. 22, in embodiments, the plane ultrasound beams and the focused ultrasound beams may be transmitted in at least three ultrasound propagation directions according to corresponding repetitive processes, which will not be described in detail herein.

In addition, in another embodiment, a two-dimensional array probe may be used. With reference to the transmitting sequence in FIG. 22B, inserting the focused ultrasound beam transmitting processes between the plane ultrasound beam transmitting processes may include repeatedly perform following steps:

first, performing a delay control on the row linear array transducer groups of the part or all of the ultrasound wave transmitting transducers in the longitudinal direction according to a first delay control strategy such that all of the column linear array transducer groups may transmit plane ultrasound beams having a first steered angle, which may be used to form a first scanning body at least once in the space in which the scanning target 12 is located;

then, performing a delay control on the column linear array transducer groups of the part or all of the ultrasound wave transmitting transducers in the transverse direction according to a third delay control strategy such that all of the row linear array transducer groups may transmit plane ultrasound beams having a second steered angles, which may be used to form a second scanning body at least once in the space in which the scanning target 12 is located;

thereafter, performing a delay control on the row linear array transducer groups of the part or all of the ultrasound wave transmitting transducers in the longitudinal direction according to a second delay control strategy such that all of the column linear array transducer groups may transmit plane ultrasound beams having a third steered angle, which may be used to form a third scanning body at least once in the space in which the scanning target 12 is located; and next, transmitting focused ultrasound beams at least once towards the scanning target.

In the embodiment above, the transmitting in three ultrasound propagation directions may be implemented. Further, in order to implement symmetrical transmitting, the first delay control strategy and the second delay control strategy may be used to obtain resultant ultrasound beams which have the same steered angle $\phi$ and of which the difference between the rotation angles $\theta$ is 180 degree.

In addition, based on the embodiments above, in one embodiment, a two-dimensional array probe may be used. With reference to the transmitting sequence in FIG. 22D, inserting the focused ultrasound beam transmitting processes between the plane ultrasound beam transmitting processes may include repeatedly perform following steps:

first, performing a delay control on the row linear array transducer groups of the part or all of the ultrasound wave transmitting transducers in the longitudinal direction according to a first delay control strategy such that all of the column linear array transducer groups may transmit plane ultrasound beams having a first steered angle, which may be used to form a first scanning body at least once in the space in which the scanning target 12 is located;

second, performing a delay control on the column linear array transducer groups of the part or all of the ultrasound wave transmitting transducers in the transverse direction according to a third delay control strategy such that all of the row linear array transducer groups may transmit plane ultrasound beams having a second steered angles, which may be used to form a second scanning body at least once in the space in which the scanning target 12 is located;

third, transmitting focused ultrasound beams at least once towards the scanning target;

fourth, performing a delay control on the row linear array transducer groups of the part or all of the ultrasound wave transmitting transducers in the longitudinal direction according to a second delay control strategy such that all of the column linear array transducer groups may transmit plane ultrasound beams having a third steered angle, which may be used to form a third scanning body at least once in the space in which the scanning target 12 is located;

fifth, performing a delay control on the column linear array transducer groups of the part or all of the ultrasound wave transmitting transducers in the transverse direction according to a fourth delay control strategy such that all of the row linear array transducer groups may transmit plane ultrasound beams having a fourth steered angles, which may be used to form a fourth scanning body at least once in the space in which the scanning target 12 is located; and sixth, transmitting focused ultrasound beams at least once towards the scanning target.

In the embodiment above, the transmitting in four ultrasound propagation directions may be implemented. Further, in order to implement symmetrical transmitting, the first delay control strategy and the second delay control strategy may be used to obtain resultant ultrasound beams which have the same steered angle $\phi$ and of which the difference between the rotation angles $\theta$ is 180 degree, and the third delay control strategy and the fourth delay control strategy may also be used to obtain resultant ultrasound beams which have the same steered angle $\phi$ and of which the difference between the corresponding rotation angles $\theta$ is 180 degree. For example, as shown in FIG. 17, the first scanning body may be formed by scanning planes 18, the second scanning body may be formed by scanning planes 12, the third scanning body may be formed by scanning planes 10, and the fourth scanning body may be formed by scanning planes 19.

Similarly, with reference to the embodiments in which the two-dimensional array probe is excited respectively in transverse and longitudinal directions and the transmitting sequence in FIG. 22, in embodiments, the plane ultrasound beams and the focused ultrasound beams may be transmitted in at least three ultrasound propagation directions according to corresponding repetitive processes, which will not be described in detail again herein. Of course, in the embodiments above, the order of the transmitting steps of the plane ultrasound beams in each repetitive process may be interchangeable. For example, the delay control may be performed on the column linear array transducer groups of the part or all of the ultrasound wave transmitting transducers in the transverse direction respectively according to the third and fourth delay control strategies first, and then the delay control may be performed on the row linear array transducer groups of the part or all of the ultrasound wave transmitting transducers in the longitudinal direction respectively according to the first and second delay control strategies, between which the focused ultrasound beam transmitting may be inserted.

As another example, the delay control may be performed on the row linear array transducer groups of the part or all of the ultrasound wave transmitting transducers in the longitudinal direction respectively according to the first and second delay control strategies first, and then the delay control may be performed on the column linear array transducer groups of the part or all of the ultrasound wave transmitting transducers in the transverse direction respectively according to the third and fourth delay control strategies, between which the focused ultrasound beam transmitting may be inserted.

In the embodiments above, independent focused ultrasound beam transmitting processes may be inserted between the plane ultrasound beam transmitting. Therefore, as shown in FIG. 19A to 19E, when the focused ultrasound beam is transmitted according to the second transmitting step, it may have directionality with a certain angle. Of course, the present disclosure will not be limited to this one technique. Another replacement insertion for inserting focused ultrasound beam transmitting processes by which at least one second transmitting step may be inserted between the processes of transmitting a plane ultrasound beams in at least three ultrasound propagation directions towards the scanning target will be described in detail below.

Figure 23A:
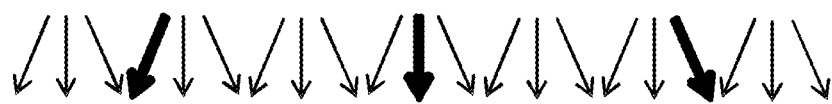
FIG. 23A and FIG. 23B schematically show techniques for inserting the focused ultrasound beam transmitting between a plurality of plane ultrasound beam transmitting by replacement.
Figure 23B:

Based on the embodiments above, in one embodiment, the third transmitting process of transmitting a plane ultrasound beams towards the scanning target in each ultrasound propagation direction may include a plurality of third transmitting steps of transmitting a plane ultrasound beam towards the scanning target. When the third transmitting steps are alternatively performed according to different ultrasound propagation directions, one third transmitting step may be replaced by one second transmitting step. As shown in FIGS. 23A and 23B, the execution order may be from left to right, one thin solid arrow may represent one third transmitting step used for transmitting a plane ultrasound beam, one thick solid arrow may represent one second transmitting step used for transmitting focused ultrasound beam, and the thin solid arrows and the thick solid arrows with different directions may represent the third transmitting steps or the second transmitting steps performed in different ultrasound propagation directions. FIGS. 23A and 23B respectively show that three second transmitting steps has replaced the third transmitting steps at corresponding positions. In FIGS. 23A and 23B, the third transmitting step may be performed at least twice in at least three ultrasound propagation directions between two adjacent second transmitting steps. With this kind of replacement insertion for inserting the focused ultrasound beam transmitting process, the echo signals of the replaced plane ultrasound beams will lose. Therefore, during the subsequent image processing, the image data corresponding to the echo signals of the plane ultrasound beams replaced by the focused ultrasound beams may be obtained by interpolation of previous and subsequent one or more frames of image data in a same ultrasound propagation direction. Herein, the image data in a same ultrasound propagation direction may be obtained using the plane beam echo signals corresponding to the same ultrasound propagation direction. Therefore, in the case that the process of inserting focused ultrasound beam transmitting processes according to the present embodiment is used, the ultrasound imaging method of the present embodiment may further include: obtaining a plurality of frames of image data before and after the moment of the replaced third transmitting step based on the ultrasound propagation direction of the replaced third transmitting step and corresponding plane beam echo signals, restoring the image data at the moment of the replaced first transmitting step by interpolation using the plurality of frames of image data, and obtaining the velocity component of the target point in the scanning target in the ultrasound propagation direction of the replaced first transmitting step using the restored image data.

Figure 24:
FIG. 24 schematically shows a technique for inserting the focused ultrasound beam transmitting in one embodiment in which the plane ultrasound beams are transmitted in four ultrasound propagation directions.
Figure 25A:
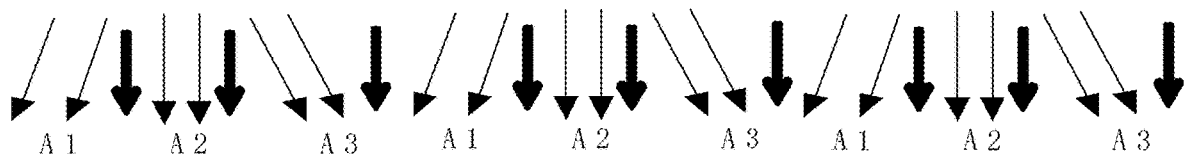
FIG. 25A, FIG. 25B, FIG. 25C, and FIG. 25D schematically show techniques for inserting the focused ultrasound beam transmitting based on the embodiments shown in FIG. 19A and FIG. 19B.
Figure 25B:
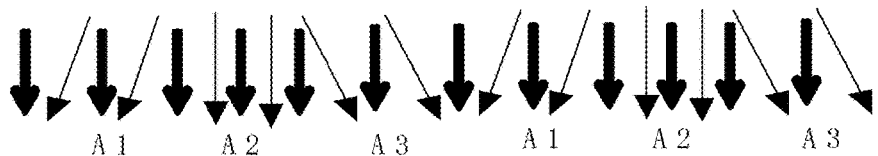
Figure 25C:
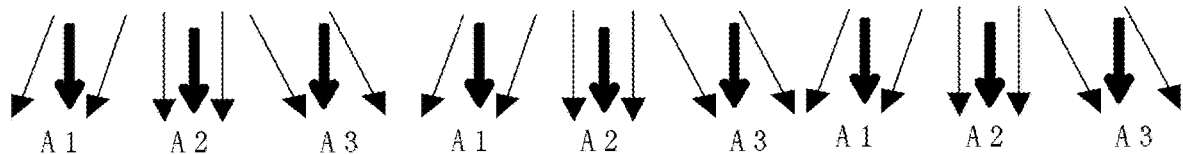
Figure 25D:
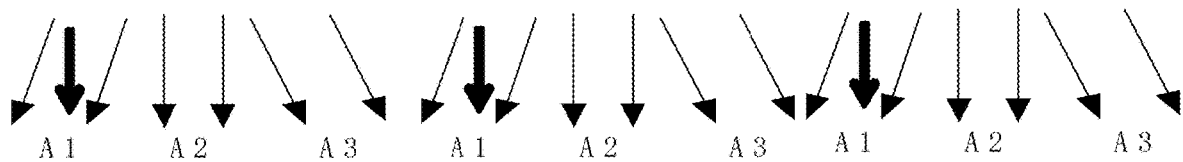

Based on the embodiments above, in one embodiment, the third transmitting step used for transmitting the plane ultrasound beam towards the scanning target may be performed at least once respectively in at least two ultrasound propagation directions between two second transmitting steps. As shown in FIG. 24, the execution order may be from left to right, the thin solid arrows may represent exciting the transducers arranged in a first direction to perform the third transmitting steps with two steered angles towards the scanning target, the dotted arrows may represent exciting the transducers arranged in a second direction to perform the third transmitting steps with two steered angles towards the scanning target, and the thin solid arrows and the dotted arrows with different directions may represent the third transmitting steps performed in different ultrasound propagation direction. One thick solid arrow may represent one second transmitting step used for transmitting the focused ultrasound beam. In the embodiment shown in FIG. 24, the third transmitting step may be performed for a plurality of times in four ultrasound propagation directions. In the embodiment shown in FIG. 24, between two second transmitting steps, two third transmitting steps respectively in two ultrasound propagation directions, and one third transmitting step respectively in two ultrasound propagation directions, may be performed. In another embodiment, during the replacement insertion for inserting the focused ultrasound beam transmitting processes, at least two third transmitting steps used for transmitting a plane ultrasound beam towards the scanning target may be performed respectively in at least three ultrasound propagation directions between two second transmitting steps. Accordingly, it can be ensured that the plane ultrasound beam echo signals used for performing the shortest calculation period of target point velocity vector once can be obtained between the two processes of transmitting the focused ultrasound beams.

Based on the embodiments above, in one embodiment, the total number of the third transmitting steps used for transmitting a plane ultrasound beams towards the scanning target corresponding to different ultrasound propagation directions between the two adjacent second transmitting steps may be same, i.e., the second transmitting steps may be evenly inserted between the processes of transmitting a plane ultrasound beams towards the scanning target in at least three ultrasound propagation directions. For example, in FIG. 22A, there may be nine third transmitting steps between two adjacent second transmitting steps; in FIG. 22B, there may be three third transmitting steps between two adjacent second transmitting steps; in FIG. 22D, there may be two third transmitting steps between two adjacent second transmitting steps; and, in FIG. 22C and FIG. 23, there may both be six third transmitting steps between two adjacent second transmitting steps. The six third transmitting steps shown in FIG. 22C and FIG. 23 may include the third transmitting step of transmitting a plane ultrasound beams towards the scanning target in different ultrasound propagation directions between the two adjacent second transmitting steps. Accordingly, the focused ultrasound beam transmitting processes may be evenly inserted between the processes of transmitting a plane ultrasound beams in a plurality of ultrasound propagation directions. Thereby, the moment of the image data to be restored may be accurately positioned during subsequent interpolation calculation of the image data, the computing speed of the computer may be increased, and the computational complexity of the image processing may be reduced.

After the velocity vector of the target point in the scanning target and the ultrasound image of at least a portion of the scanning target are obtained, in step 708, the velocity vector and the ultrasound image may be displayed. For example, the velocity vector and the ultrasound image may be displayed on the display 8 simultaneously. For example, in one embodiment, the velocity vector may be superposed on the ultrasound image. Similarly, in order to ensure that human eye can comfortably sense the velocity vector, the velocity vector may be slowed down before it is displayed.

FIG. 7 and/or FIG. 21 show a flow chart of an ultrasound imaging method according to one embodiment. It should be understood that, although the steps of the flow chart in FIG. 7 and/or FIG. 21 are successively shown according to the indication of the arrows, there steps will not necessarily be performed successively in the order indicated by the arrows. Unless expressly stated in the present disclosure, the order of performing these steps will not be strictly limited. Rather, other order may also be possible. Furthermore, at least a part of the steps in FIG. 7 and/or FIG. 21 may include a plurality of sub-steps or stages. The sub-steps or stages may not be necessarily done at the same time, but may be performed at different moments. They also may not necessarily be performed successively, but may be alternately performed with other steps or at least a part of the sub-steps or stages of other steps. In the description of the embodiments above, only the implement of the steps in FIG. 7 and/or FIG. 21 is described. However, in the case of no contradiction in logic, the embodiments above may be combined with each other to form new technical solutions, which will still fall into the scope of the embodiments.

Through the description of the embodiments above, a person skilled in the art can easily understand that the methods in the embodiments above can be implemented by software and general hardware platform, or can also be implemented by hardware. Based on such understanding, the essence, or the parts contributing to the art, of the technical solutions may be implemented as software products. The software products may be carried by a non-volatile computer-readable storage medium (e.g., ROM, disk, optical disc), and may include a plurality instructions which may be used to instruct a processor within a terminal device (such as cell phone, computer, sever or network equipment, etc.) to implement the system structures and methods of the embodiments.

Based on the ultrasound imaging methods above, an ultrasound imaging system may also be provided by the present disclosure. The system may include:

a probe 1;

a transmitting circuit 2 which may excite the probe 1 to transmit ultrasound beams towards the scanning target in at least three ultrasound propagation directions, where the transmitting circuit 2 may excite a part or all of the ultrasound wave transmitting transducers in the probe 1 to transmit ultrasound beams towards the scanning target in at least three ultrasound propagation directions to form at least three scanning bodies, or, the transmitting circuit 2 may divide the probe 1 into a plurality of transducer regions and excite a part or all of the transducer regions to transmit ultrasound beams towards the scanning target in at least three ultrasound propagation directions to form at least three scanning bodies, where each scanning body may be derived from the ultrasound beams transmitted in one ultrasound propagation direction;

a receiving circuit 4 and a beamforming unit 5 which may receive the echoes of the ultrasound beams to obtain at least three groups of echo signals, where each group of echo signals may be derived from the ultrasound beams transmitted in one ultrasound propagation direction. Specifically, the step of transmitting the ultrasound beams towards the scanning target may be performed at least twice in each ultrasound propagation direction, each group of echo signals may include at least two echo signal each of which may be derived from the echoes obtained by performing the step of transmitting the ultrasound beams towards the scanning target for one time in one ultrasound propagation direction;

a data processing unit 9 which may calculate one velocity component of the target point in the scanning target using one of the at least three groups of echo signals to obtain at least three velocity components using the at least three groups of echo signals, and obtain the velocity vector of the target point using the at least three velocity components, where the at least three ultrasound propagation directions corresponding to the at least three groups of echo signals used for calculating the at least three velocity components may be not in a same plane. The data processing unit 9 may also obtain the ultrasound image of at least a portion of the scanning target; and a display 8 which may display the velocity vector and the ultrasound image.

Based on the embodiments above, as shown in FIG. 1, in one embodiment, the data processing unit 9 may include a signal processing unit 6 and/or a image processing unit 7. The signal processing unit 6 may perform the calculation processes related to the velocity components and the velocity vector, i.e., step 300 and step 400 above, and the image processing unit 7 may perform the processes related to image processing, i.e., step 500 above. The transmitting circuit 2 may perform step 100 above, and the receiving circuit 4 and the beamforming unit 5 may perform step 200 above. The specific implement of the various units may be similar to the specific description of the various steps above and will not be described in detail again herein.

Based on the embodiments above, in one embodiment, the transmitting circuit 2 may also excite the probe 1 to transmit focused ultrasound beams towards the scanning target. At least one step of transmitting the focused ultrasound beams toward the scanning target may be inserted between the processes of transmitting the ultrasound beams towards the scanning target in at least three ultrasound propagation directions. Furthermore, the receiving circuit 4 and the beamforming unit 5 may receive the echoes of the focused ultrasound beams to obtain focused ultrasound beam echo signals. The data processing unit 9 may obtain ultrasound images using the focused ultrasound beam echo signals. In another embodiment, the data processing unit 9 may also obtain the ultrasound images using the at least three groups of echo signals. The specific implement of the processes above may be similar to the detailed description with respect to step 100 above and will not be described again herein.

Based on the embodiments above, in one embodiment, the data processing unit may further obtain the number of the ultrasound propagation directions or the number of the velocity components to be used for synthesizing the velocity vector selected by the user and generate an instruction, adjust the number of the ultrasound propagation directions according to the instruction, and determine the number of the velocity components to be used for synthesizing the velocity vector or adjust the number of the velocity components to be used for synthesizing the velocity vector of the target point according to the number of the ultrasound propagation directions.

Based on the embodiments above, in one embodiment, during the transmitting circuit 2 exciting the probe 1 to transmit ultrasound beams towards the scanning target point in at least three ultrasound propagation directions, adjacent at least three ultrasound propagation directions may not be in a same plane. The data processing unit 9 may calculate the velocity components of the target point in at least three ultrasound propagation directions corresponding to the at least three groups of echo signals received successively and synthesize the velocity vector of the target point using the velocity components in the at least three ultrasound propagation directions. In another embodiment, during the transmitting circuit 2 exciting the probe 1 to transmit the ultrasound beams towards the scanning target in at least three ultrasound propagation directions, all of the ultrasound propagation directions may not be in a same plane. The data processing unit 9 may calculate the velocity components of the target point in all of the ultrasound propagation directions corresponding to the at least three groups of echo signals and synthesize the velocity vector of the target point using the velocity components in all of the ultrasound propagation directions. The specific implement of the processes above may be similar to the detailed description with respect to step 100 above and will not be described again herein.

In the embodiments above, a technique for the transmitting circuit 2 to excite the probe 1 to transmit the ultrasound beams towards the scanning target in at least three ultrasound propagation directions may be similar to the related detailed description above and will not be described again herein.

Of course, the present disclosure will not be limited to implementing the specific ultrasound beam transmitting using the two-dimensional array probe. For example, it may also be implemented using the linear array probe, as mentioned above. In this case, a driving mechanism may be provided to adjust the spatial position of the ultrasound wave transmitting transducers in the probe. The driving mechanism may drive the ultrasound wave transmitting transducers in the probe to move or rotate to desired spatial position according to predetermined ultrasound propagation direction in order to form the scanning bodies obtained in different ultrasound propagation directions mentioned above. Thereby, the processes of transmitting the ultrasound beams towards the scanning target in at least three ultrasound propagation directions may be implemented.

In the ultrasound imaging methods and the ultrasound imaging system provided by the present disclosure, both the plane ultrasound beams and the focused ultrasound beams can be used during the imaging. The plane ultrasound beams may be used to obtain the velocity vectors, and thereby the advantage of the high frame rate of plane ultrasound beam imaging may be fully utilized to satisfy the high frame rate requirement of the fluid velocity measurement using ultrasound imaging. The focused ultrasound beams may be used to obtain the ultrasound images of the scanning target, and thereby the advantages of high signal-to-noise ratio of the echo signal, high quality of obtained ultrasound images and high lateral resolution of focused ultrasound beam imaging may be fully used to obtain better images for observation of the user. Accordingly, not only high accuracy, high real-time and high frame rate three-dimensional velocity vectors which are close to actual velocity, but also the images (e.g., B mode images) with high quality may be obtained. Thereby, when the velocity vectors (e.g., the velocity vectors of the blood) are shown, the surrounding organs, such as the tissue and vascular wall, etc., can still be clearly displayed in the grayscale images.

Furthermore, in some embodiments, the plane ultrasound beams and the focused ultrasound beams may be transmitted alternately, i.e., the focused ultrasound beam transmitting may be discretely inserted between the plane ultrasound beam transmitting. Accordingly, not only the continuity of the velocity vectors, but also the synchronization of the velocity vectors with the ultrasound images (e.g., B mode images) may be ensured.

The embodiments disclosed above should not be interpreted as limitations to the scope of the present invention. Many modifications and improvements may be made by a person of skill in the art without departing from the concepts disclosed herein. Therefore, the scope of protection of the present invention should be defined by the claims.

The invention claimed is:

1. An ultrasound imaging method, comprising:
   transmitting, via a probe, ultrasound beams towards a scanning target in at least three ultrasound propagation directions to form at least three scanning bodies, wherein the at least three scanning bodies include an overlapping region in space, and each of the scanning bodies is derived from the ultrasound beams transmitted in a respective one of the at least three ultrasound propagation directions;
   receiving, via a receiving circuit, echoes of the ultrasound beams returned by the at least three scanning bodies and converting the echoes into electric signals;
   beamforming, via a beamforming unit, the electric signals to obtain at least three groups of echo signals, wherein each group of echo signals is derived from ultrasound beams transmitted in one ultrasound propagation direction;
   calculating, via a data processing unit, velocity vectors of multiple target points using the at least three groups of echo signals, wherein the multiple target points are points covered by the overlapping region in the scanning target, and a velocity vector of any of the multiple target points is obtained by:
   calculating, via the data processing unit, at least three velocity components of the any of the multiple target points using the at least three groups of echo signals, wherein one velocity component of the any of the multiple target points is calculated using one group of echo signals of the at least three groups of echo signals; and
   synthesizing, via the data processing unit, a velocity vector of the any of the multiple target points using the at least three velocity components, wherein the at least three ultrasound propagation directions corresponding to the at least three groups of echo signals used for calculating the at least three velocity components are not in a same plane;
   obtaining an ultrasound image of at least a portion of the scanning target; and
   displaying, via a display, the ultrasound image and the velocity vectors of the multiple target points.

2. The ultrasound imaging method of claim 1, wherein the ultrasound beams are transmitted towards the scanning target alternately according to different ultrasound propagation directions.

3. The ultrasound imaging method of claim 1, wherein, the ultrasound beams are transmitted towards the scanning target at least two times in each ultrasound propagation direction, and each group of echo signals comprises at least two echo signals each of which is derived from echoes obtained by transmitting the ultrasound beam towards the scanning target one time in one ultrasound propagation direction.

4. The ultrasound imaging method of claim 1, wherein obtaining the ultrasound image of at least a portion of the scanning target comprises:
   obtaining, via the data processing unit, the ultrasound image using the at least three groups of echo signals.

5. The ultrasound imaging method of claim 4, wherein at least one transmission of a focused ultrasound beams towards the scanning target is inserted between the transmitting of the ultrasound beams towards the scanning target in the at least three ultrasound propagation directions.

6. The ultrasound imaging method of claim 1, wherein transmitting the ultrasound beams towards the scanning target in the at least three ultrasound propagation directions to form the at least three scanning bodies comprises:
   exciting, via a transmitting circuit, a part or all of ultrasound wave transmitting transducers to transmit the ultrasound beams towards the scanning target in the at least three ultrasound propagation directions such that the ultrasound beams propagate in a space in which the scanning target is located to form at least three scanning bodies.

7. The ultrasound imaging method of claim 1, wherein transmitting the ultrasound beams towards the scanning target in the at least three ultrasound propagation directions comprises:
   dividing, via a transmitting circuit, ultrasound wave transmitting transducers into a plurality of transducer regions and exciting a part or all of the transducer regions to transmit the ultrasound beams in at least three ultrasound propagation directions.

8. The ultrasound imaging method of claim 3, wherein the velocity component is calculated one time after the ultrasound beam towards the scanning target is transmitted at least two times in each ultrasound propagation direction.

9. The ultrasound imaging method of claim 2, wherein ultrasound propagation directions for at least three successive transmissions are not in a same plane.

10. The ultrasound imaging method of claim 9, wherein calculating the at least three velocity components of the any of the multiple target points using the at least three groups of echo signals and synthesizing the velocity vector of the any of the multiple target points using the at least three velocity components comprises:
    calculating velocity components of the any of the multiple target points in at least three ultrasound propagation directions corresponding to at least three groups of echo signals received successively; and
    synthesizing the velocity vector of the any of the multiple target points using the velocity components in the at least three ultrasound propagation directions.

11. The ultrasound imaging method of claim 1, wherein calculating the at least three velocity components of the any of the multiple target points using the at least three groups of echo signals and synthesizing the velocity vector of the any of the multiple target points using the at least three velocity components comprises:
    calculating velocity components of the any of the multiple target points in all ultrasound propagation directions corresponding to the at least three groups of echo signals; and
    synthesizing the velocity vector of the any of the multiple target points using the velocity components in all ultrasound propagation directions.

12. The ultrasound imaging method of claim 1, further comprising:
    obtaining, via the data processing unit, number of the ultrasound propagation directions or number of velocity components to be used for synthesizing the velocity vector selected by user to generate an instruction; and
    adjusting, via the data processing unit, the number of the ultrasound propagation directions according to the instruction and determining the number of velocity components to be used for synthesizing the velocity vector or adjusting the number of velocity components to be used for synthesizing the velocity vector of the any of the multiple target points according to the number of the ultrasound propagation directions.

13. An ultrasound imaging method, comprising:
transmitting, via a probe, plane ultrasound beams towards a scanning target in at least three ultrasound propagation directions to form at least three scanning bodies, wherein the at least three scanning bodies include an overlapping region in space, and each of the scanning bodies is derived from the plane ultrasound beams transmitted in a respective one of the at least three ultrasound propagation directions;
receiving, via a receiving circuit, echo signals of the plane ultrasound beams returned by the at least three scanning bodies and converting the echoes into electric signal;
beamforming, via a beamforming unit, the electric signals to obtain at least three groups of plane beam echo signals, wherein each group of plane beam echo signals is derived from plane ultrasound beams transmitted in one ultrasound propagation direction;
calculating, via a data processing unit, velocity vectors of multiple target points using the at least three groups of echo signals, wherein the multiple target points are points covered by the overlapping region in the scanning target, and a velocity vector of any of the multiple target points is obtained by:
calculating, via the data processing unit, at least three velocity components of the any of the multiple target points using the at least three groups of plane beam echo signals, wherein one velocity component of the any of the multiple target points is calculated using one group of plane beam echo signals of the at least three groups of plane beam echo signals; and
synthesizing, via the data processing unit, a velocity vector of the any of the multiple target points using the at least three velocity components, wherein at least three ultrasound propagation directions corresponding to the at least three groups of plane beam echo signals used for calculating the at least three velocity components are not in a same plane;
transmitting, via the probe, focused ultrasound beams towards the scanning target;
receiving, via the receiving circuit, echoes of the focused ultrasound beams and converting the echoes into electric signals;
beamforming, via a beamforming unit, the electric signals to obtain the focused ultrasound beam echo signals;
obtaining, via the data processing unit, an ultrasound image of at least a portion of the scanning target using the focused ultrasound beam echo signals; and
displaying, via a display, the ultrasound image and the velocity vectors of the multiple target points.

14. The ultrasound imaging method of claim 13, wherein the plane ultrasound beams are transmitted towards the scanning target alternately in different ultrasound propagation directions.

15. The ultrasound imaging method of claim 14, wherein at least one transmission of the focused ultrasound beams towards the scanning target is inserted between the transmitting of the plane ultrasound beams towards the scanning target in the at least three ultrasound propagation directions.

16. The ultrasound imaging method of claim 13, wherein, transmitting focused ultrasound beams towards the scanning target comprises transmitting focused ultrasound beam towards the scanning target a plurality of times, transmitting the plane ultrasound beams towards the scanning target comprises transmitting the plane ultrasound beams towards the scanning target at least two times in each ultrasound propagation direction, and each group of plane beam echo signals comprises at least two plane beam echo signals each of which is derived from echoes obtained by transmitting the a plane ultrasound beam towards the scanning target one time in one ultrasound propagation direction.

17. The ultrasound imaging method of claim 13, wherein transmitting the plane ultrasound beams towards the scanning target in at least three ultrasound propagation directions comprises:
exciting, via a transmitting circuit, a part or all of ultrasound wave transmitting transducers to transmit plane ultrasound beams towards the scanning target in at least three ultrasound propagation directions.

18. The ultrasound imaging method of claim 16, wherein the velocity component is calculated one time after the plane ultrasound beams towards the scanning target is transmitted at least two times in each ultrasound propagation direction.

19. The ultrasound imaging method of claim 14, wherein ultrasound propagation directions for at least three successive transmissions are not in a same plane.

20. The ultrasound imaging method of claim 19, wherein calculating at least three velocity components of the any of the multiple target points using the at least three groups of echo signals and synthesizing the velocity vector of the any of the multiple target points using the at least three velocity components comprises:
calculating velocity components of the any of the multiple target points in at least three ultrasound propagation directions corresponding to at least three groups of plane beam echo signals received successively; and
synthesizing the velocity vector of the any of the multiple target points using the velocity components in the at least three ultrasound propagation directions.

21. The ultrasound imaging method of claim 13, wherein calculating the at least three velocity components of the any of the multiple target points using the at least three groups of echo signals and synthesizing the velocity vector of the any of the multiple target points using the at least three velocity components comprises:
calculating velocity components of the any of the multiple target points in all ultrasound propagation directions corresponding to the at least three groups of plane beam echo signals; and
synthesizing the velocity vector of the any of the multiple target points using the velocity components in all ultrasound propagation directions.

22. The ultrasound imaging method of claim 13, further comprising:
obtaining, via the data processing unit, number of the ultrasound propagation directions or number of velocity components to be used for synthesizing the velocity vector selected by user to generate an instruction; and
adjusting, via the data processing unit, the number of the ultrasound propagation directions according to the instruction and determining the number of velocity components to be used for synthesizing the velocity vector or adjusting the number of velocity components to be used for synthesizing the velocity vector of the any of the multiple target points according to the number of the ultrasound propagation directions.

23. An ultrasound imaging system, comprising:
a probe;
a transmitting circuit which excites the probe to transmit ultrasound beams towards a scanning target in at least three ultrasound propagation directions to form at least three scanning bodies, wherein the at least three scanning bodies include an overlapping region in space, and each of the scanning bodies is derived from the ultrasound beams transmitted in a respective one of the at least three ultrasound propagation directions;

a receiving circuit which receives echoes of the ultrasound beams returned by the at least three scanning bodies and convert the echoes into electric signals;

a beamforming unit which beamforms the electric signals to obtain at least three groups of echo signals, wherein each group of echo signals is derived from ultrasound beams transmitted in one ultrasound propagation direction;

a data processing unit which calculates velocity vectors of multiple target points using the at least three groups of echo signals, wherein the multiple target points are points covered by the overlapping region in the scanning target, and a velocity vector of any of the multiple target points is obtained by calculating at least three velocity components of the any of the multiple target points in the scanning target using the at least three groups of echo signals, wherein, one velocity component of the any of the multiple target points is calculated using one group of echo signals of the at least three groups of echo signals, and the at least three ultrasound propagation directions corresponding to the at least three groups of echo signals used for calculating the at least three velocity components are not in a same plane; and wherein the data processing unit further obtains an ultrasound image of at least a portion of the scanning target; and a display which displays the ultrasound image and the velocity vectors of the multiple target points.

24. The ultrasound imaging system of claim 23, wherein the ultrasound beams are transmitted towards the scanning target at least two times in each ultrasound propagation direction, and each group of echo signals comprises at least two echo signals each of which is derived from echoes obtained by transmitting the ultrasound beam towards the scanning target one time in one ultrasound propagation direction.

25. The ultrasound imaging system of claim 23, wherein the ultrasound beams are transmitted towards the scanning target alternately in different ultrasound propagation directions.

26. The ultrasound imaging system of claim 23, wherein the data processing unit obtains the ultrasound image using the at least three groups of echo signals.

27. The ultrasound imaging system of claim 25, wherein, the transmitting circuit further excites the probe to transmit focused ultrasound beams towards the scanning target, wherein at least one transmission of the focused ultrasound beams towards the scanning target is inserted between the transmitting of the ultrasound beams towards the scanning target in at least three ultrasound propagation directions;

the receive circuit further receives echoes of the focused ultrasound beams and convert the echoes into electric signals;

the beamforming unit further beamforms the electric signals to obtain focused ultrasound beam echo signal; and the data processing unit further obtains the ultrasound image using the focused ultrasound beam echo signals.

28. The ultrasound imaging system of claim 23, wherein, the transmitting circuit excites a part or all of ultrasound wave transmitting transducers in the probe to transmit the ultrasound beams towards the scanning target in the at least three ultrasound propagation directions.

29. The ultrasound imaging system of claim 23, wherein, the transmitting circuit divides the probe into a plurality of transducer regions and excites a part or all of the transducer regions to transmit the ultrasound beams towards the scanning target in the at least three ultrasound propagation directions.

30. The ultrasound imaging system of claim 25, wherein, ultrasound propagation directions for at least three successive transmissions are not in a same plane; and wherein, the data processing unit calculates velocity components of the any of the multiple target points in the at least three ultrasound propagation directions corresponding to at least three groups of echo signals received successively and synthesize the velocity vector of the any of the multiple target points using the velocity components in the at least three ultrasound propagation directions.

31. The ultrasound imaging system of claim 23, wherein, all of the ultrasound propagation directions in which the ultrasound beams are transmitted towards the scanning target are not in a same plane; and wherein, the data processing unit calculates velocity components of the any of the multiple target points in all of the ultrasound propagation directions corresponding to the at least three groups of echo signals and synthesizes the velocity vector of the any of the multiple target points using the velocity components in all of the ultrasound propagation directions.

32. The ultrasound imaging system of claim 23, wherein, the data processing unit further obtains number of the ultrasound propagation directions or number of velocity components to be used for synthesizing the velocity vector selected by user to generate an instruction, and adjusts the number of the ultrasound propagation directions according to the instruction and determines the number of velocity components to be used for synthesizing the velocity vector or adjusts the number of velocity components to be used for synthesizing the velocity vector of the any of the multiple target points according to the number of the ultrasound propagation directions.

33. The ultrasound imaging method of claim 1, wherein calculating at least three velocity components of the any of the multiple target points using the at least three groups of echo signals comprises:

processing the at least three groups of echo signals to obtain three groups of three-dimensional image data acquired at a same time, and calculating the at least three velocity components of the any of the multiple target points using the three groups of three-dimensional image data.

* * * * *

UNITED STATES PATENT AND TRADEMARK OFFICE
CERTIFICATE OF CORRECTION

PATENT NO. : 10,976,422 B2
APPLICATION NO. : 15/632176
DATED : April 13, 2021
INVENTOR(S) : Yigang Du, Rui Fan and Yong Li Page 1 of 1

It is certified that error appears in the above-identified patent and that said Letters Patent is hereby corrected as shown below:

On the Title Page

Item (12) Line 2 delete "Yigang et al." and insert --Du et al.--

Inventors item (72) Line 1 delete "Du Yigang" and insert --Yigang Du--

Inventors item (72) Line 1 delete "Fan Rui" and insert --Rui Fan--

Inventors item (72) Line 2 delete "Li Yong" and insert --Yong Li--

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*